(12) United States Patent
Yamada

(10) Patent No.: US 9,565,991 B2
(45) Date of Patent: Feb. 14, 2017

(54) ADVANCE AND RETREAT ASSIST TOOL FOR ENDOSCOPIC TREATMENT INSTRUMENT

(71) Applicant: OLYMPUS CORPORATION, Tokyo (JP)

(72) Inventor: Tetsuhiro Yamada, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 128 days.

(21) Appl. No.: 14/527,140

(22) Filed: Oct. 29, 2014

(65) Prior Publication Data

US 2015/0119641 A1 Apr. 30, 2015

Related U.S. Application Data

(63) Continuation of application No. PCT/JP2014/050023, filed on Jan. 6, 2014.

(30) Foreign Application Priority Data

Feb. 27, 2013 (JP) .................................. 2013-037223

(51) Int. Cl.
    *A61B 1/00*    (2006.01)
    *A61B 1/04*    (2006.01)
    (Continued)

(52) U.S. Cl.
    CPC ....... *A61B 1/00133* (2013.01); *A61B 1/00066* (2013.01); *A61B 1/00128* (2013.01); *A61B 1/018* (2013.01); *A61B 17/00234* (2013.01); *A61B 2017/0034* (2013.01)

(58) Field of Classification Search
    USPC ........ 600/104, 106, 107, 114–115, 121–125, 600/139–152, 153, 154; 606/205–209
    See application file for complete search history.

(56) References Cited

U.S. PATENT DOCUMENTS

2006/0094927 A9* 5/2006 Okada ................ A61B 1/00133
                                                         600/101
2006/0258905 A1* 11/2006 Kaji ................... A61B 1/00133
                                                         600/106

(Continued)

FOREIGN PATENT DOCUMENTS

JP       A-9-276211      10/1997
JP       Y2-2560353      1/1998
(Continued)

OTHER PUBLICATIONS

International Search Report issued in International Application No. PCT/JP2014/050023 mailed Mar. 18, 2014.
(Continued)

*Primary Examiner* — Ryan Henderson
(74) *Attorney, Agent, or Firm* — Oliff PLC

(57) ABSTRACT

An advance and retreat assist tool includes a base unit, an attachment portion which attaches the base unit to a treatment instrument insertion portion, a tubular member provided to advance and retreat relative to the base unit coaxially with a central axis of a hole portion and a fixing portion which fixes an endoscopic treatment instrument to the tubular member. The advance and retreat assist tool further includes a rotary portion which has an axis different from an axis of the tubular member and which rotates around the axis, and an advance and retreat mechanism.

15 Claims, 25 Drawing Sheets

(51) Int. Cl.
*A61B 1/018* (2006.01)
*A61B 17/00* (2006.01)

(56) References Cited

U.S. PATENT DOCUMENTS

| | | | | |
|---|---|---|---|---|
| 2007/0255311 | A1* | 11/2007 | Hiraoka | A61B 1/00137 |
| | | | | 606/205 |
| 2008/0064920 | A1 | 3/2008 | Bakos et al. | |
| 2010/0010293 | A1* | 1/2010 | Sato | A61F 2/88 |
| | | | | 600/101 |
| 2010/0063354 | A1* | 3/2010 | Hashimoto | A61B 17/29 |
| | | | | 600/106 |
| 2010/0280311 | A1* | 11/2010 | McGrath | A61B 1/00105 |
| | | | | 600/104 |
| 2012/0029278 | A1* | 2/2012 | Sato | A61B 17/00234 |
| | | | | 600/104 |
| 2014/0171735 | A1* | 6/2014 | Galperin | A61B 1/00066 |
| | | | | 600/106 |

FOREIGN PATENT DOCUMENTS

| | | |
|---|---|---|
| JP | A-2003-265406 | 9/2003 |
| JP | A-2005-211126 | 8/2005 |
| JP | A-2008-80119 | 4/2008 |

OTHER PUBLICATIONS

Sep. 11, 2015 International Preliminary Report on Patentability issued in International Application No. PCT/JP2014/050023.

* cited by examiner

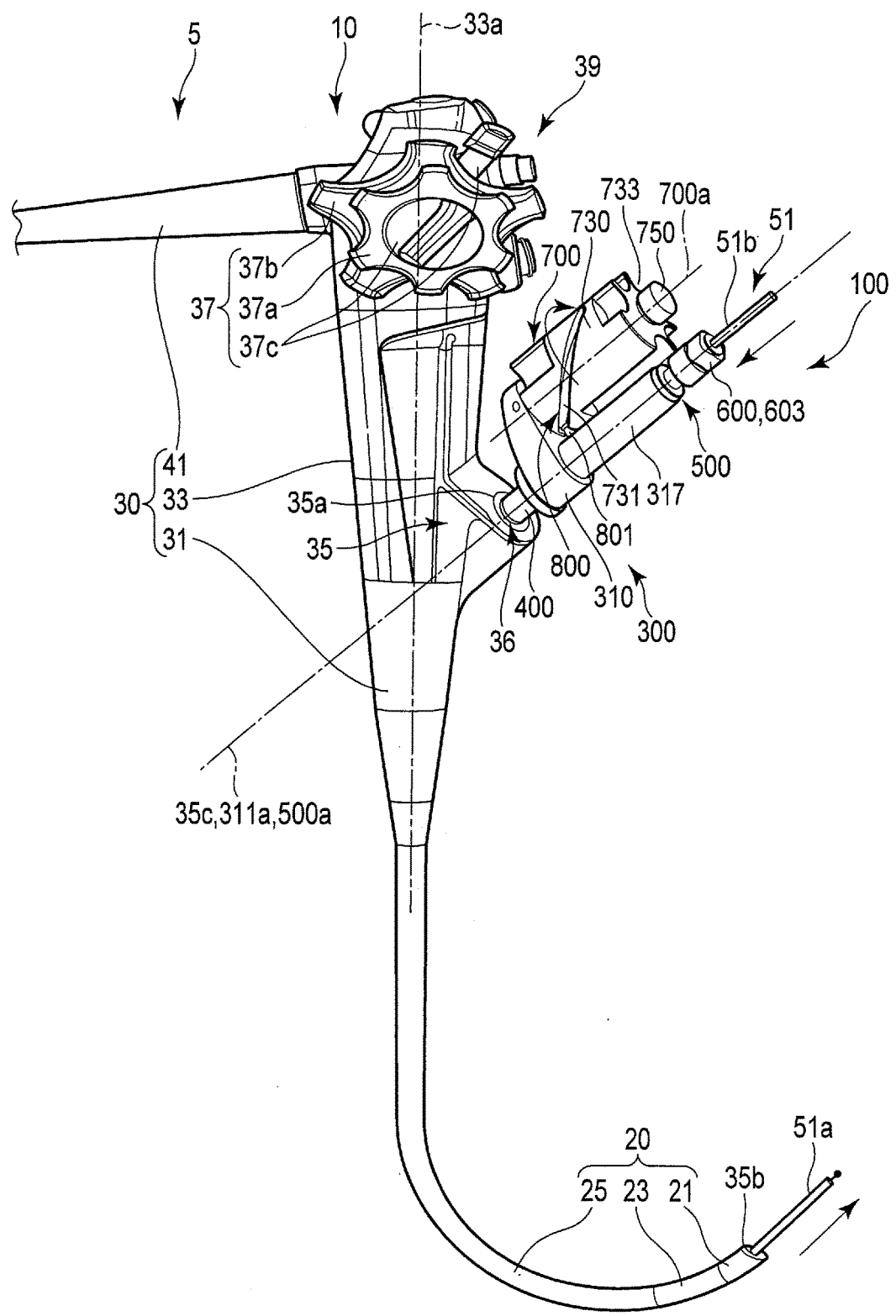
F I G. 1A

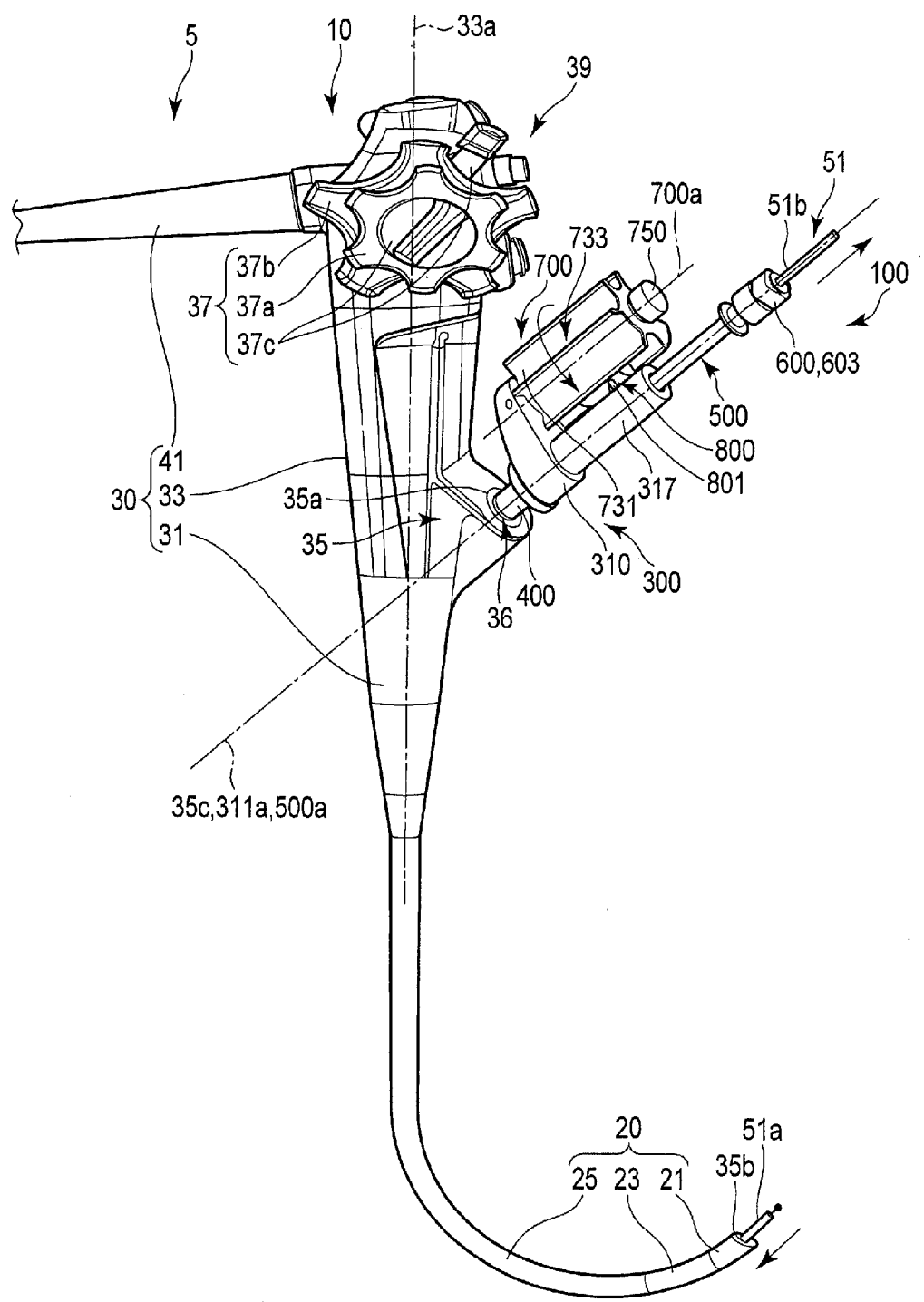
F I G. 1B

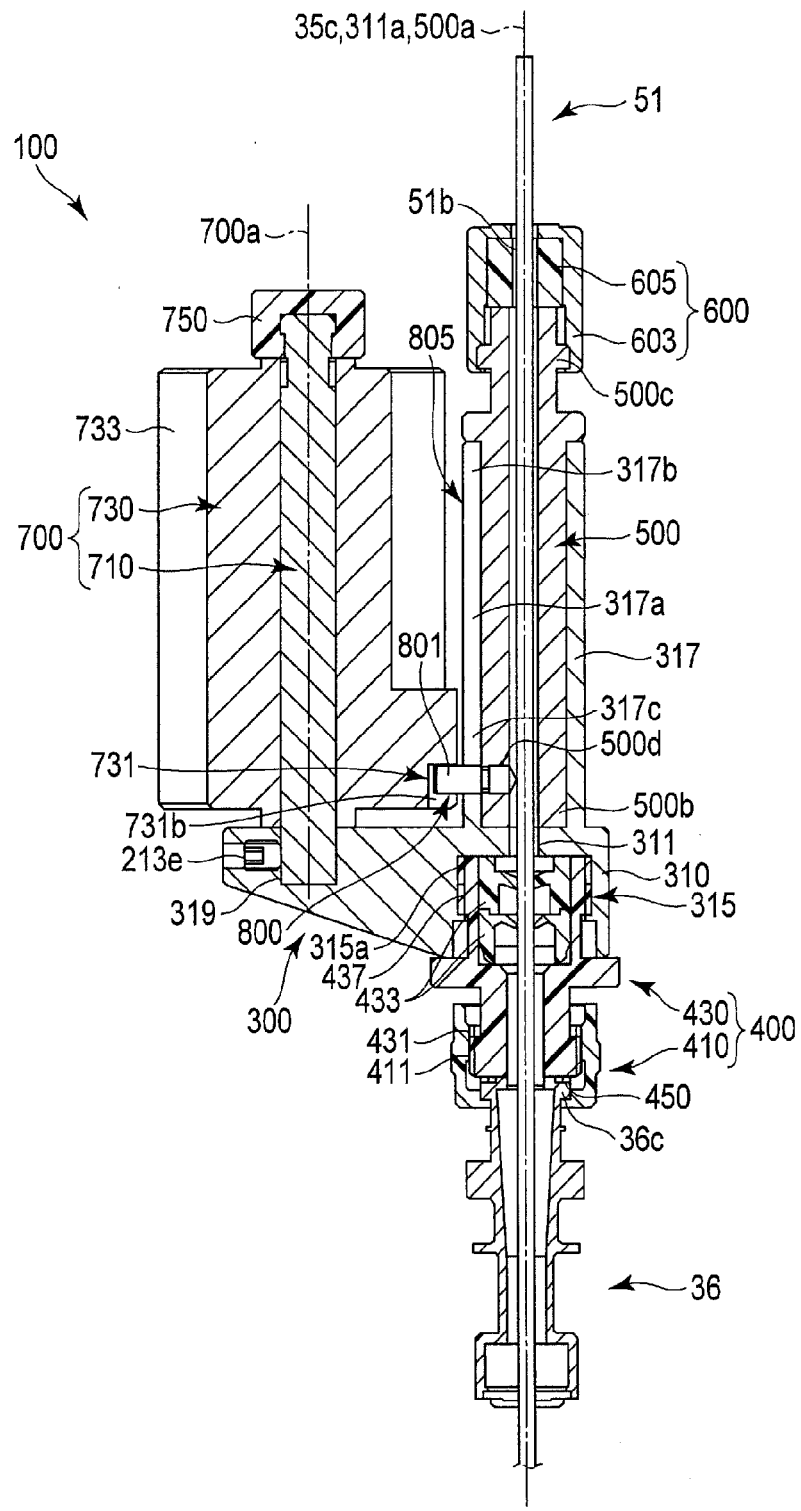
F I G. 4A

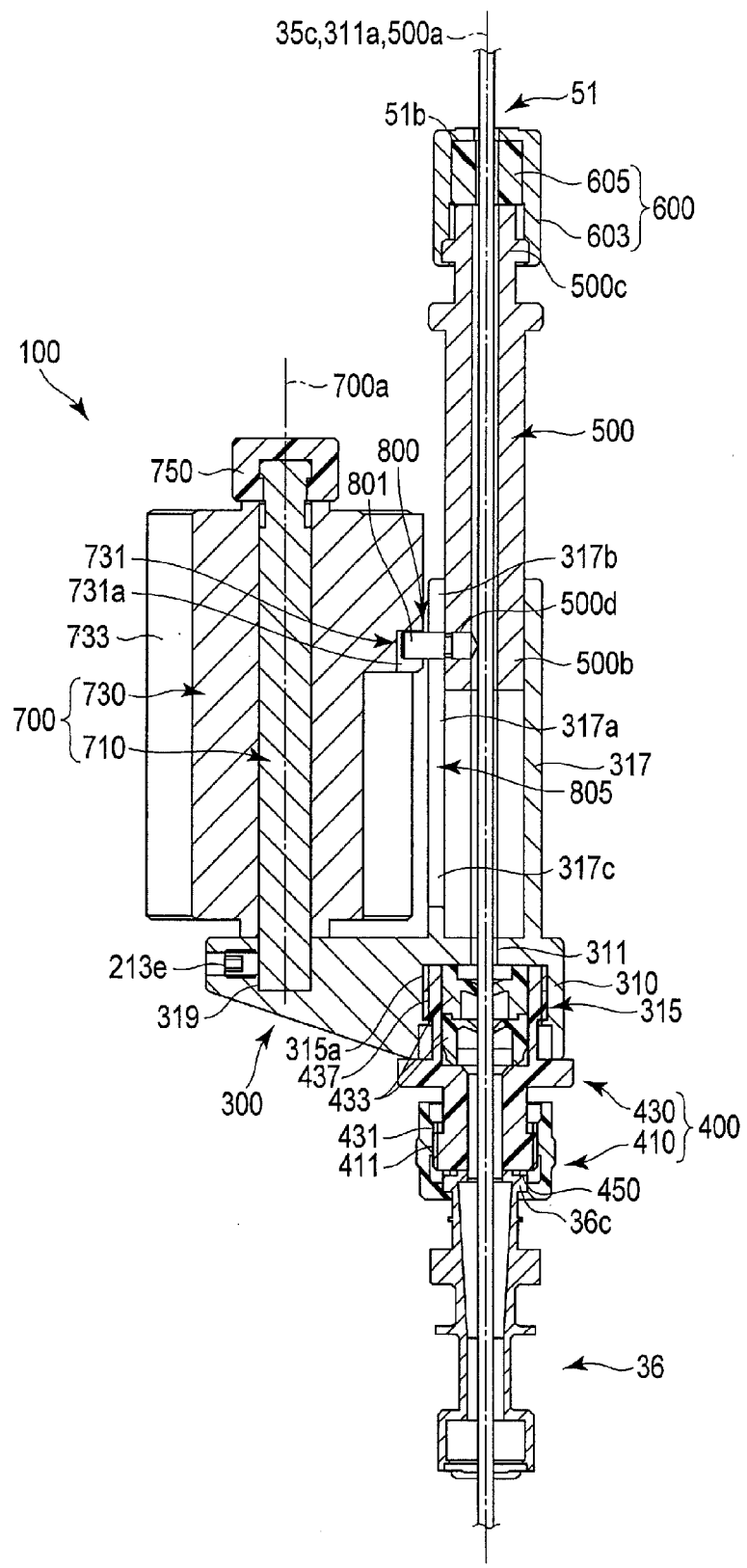
F I G. 4B

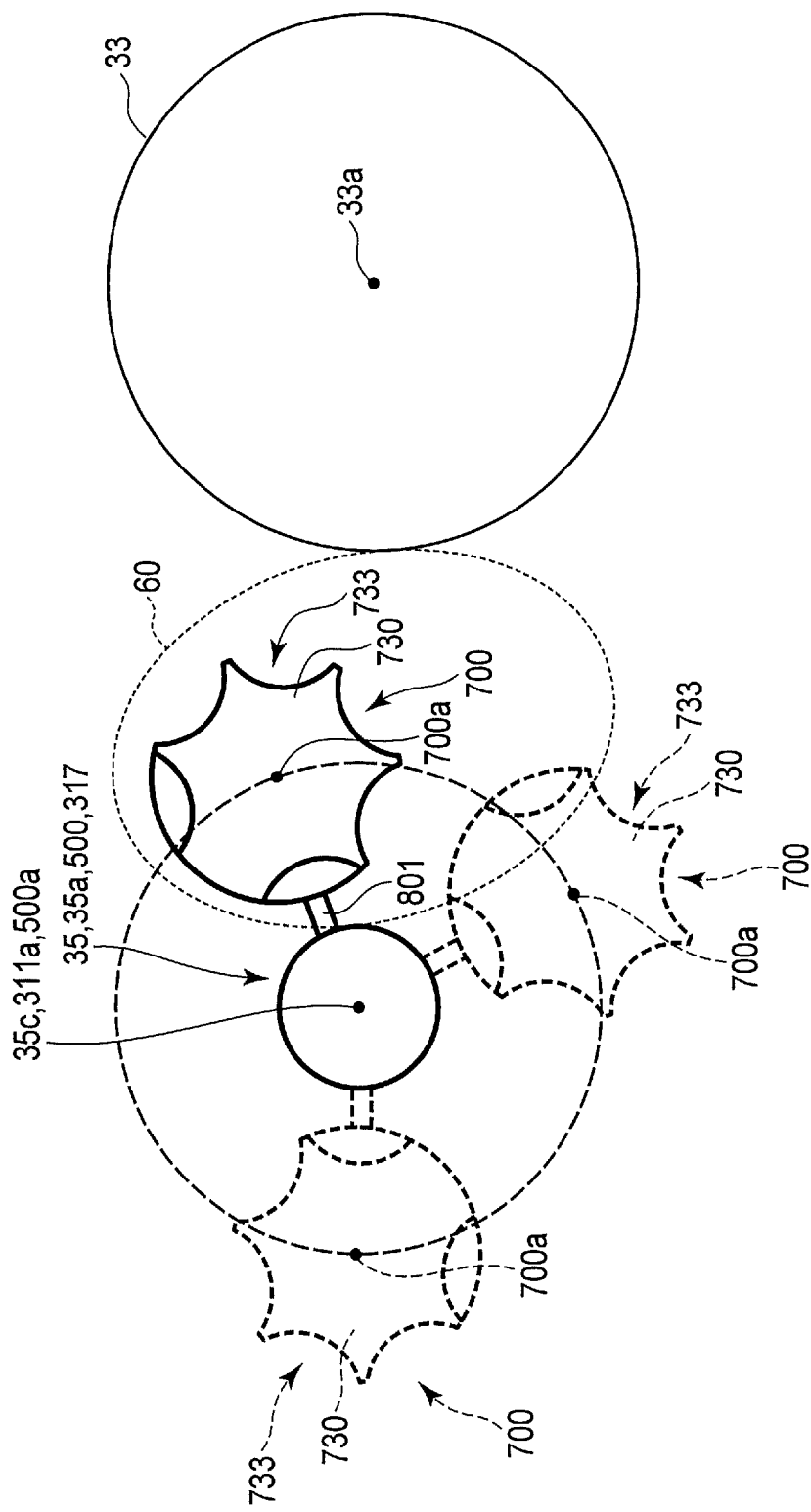
F I G. 5C

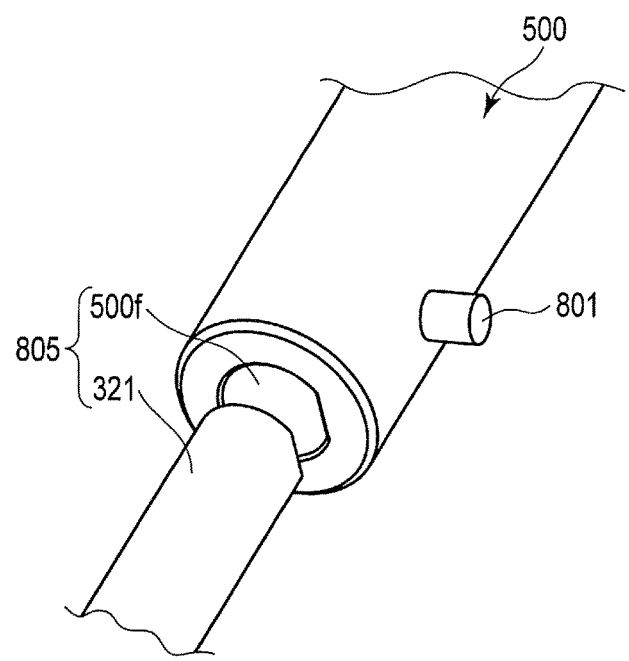
F I G. 6A
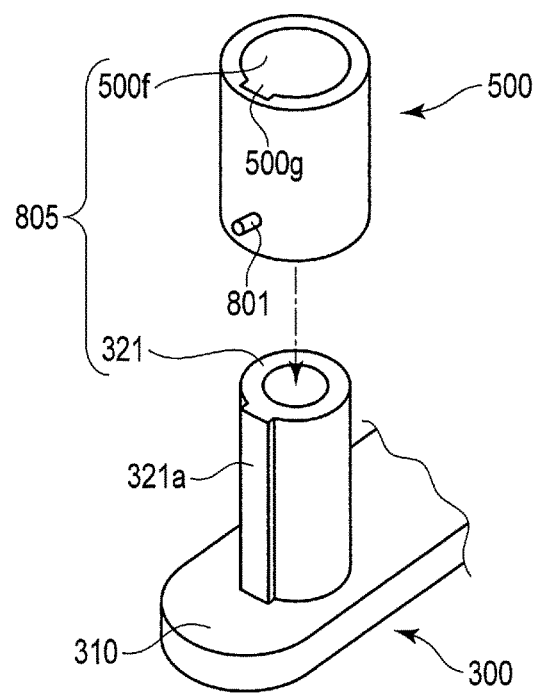
F I G. 6B

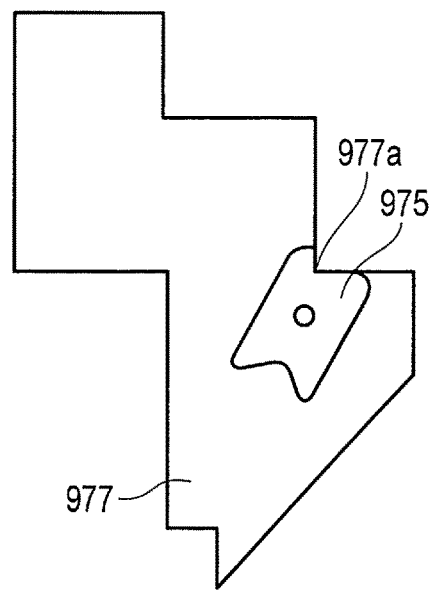
F I G. 7E
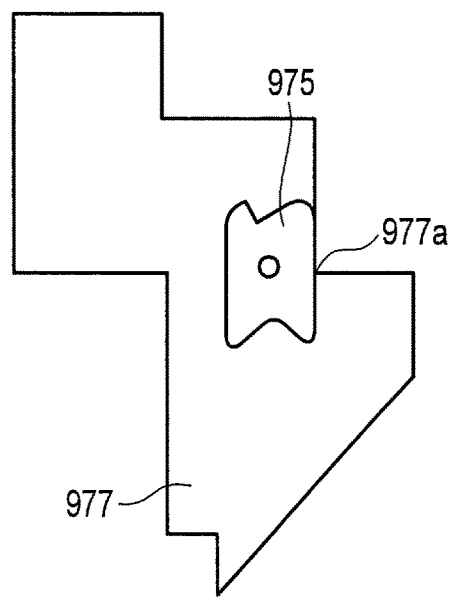
F I G. 7F

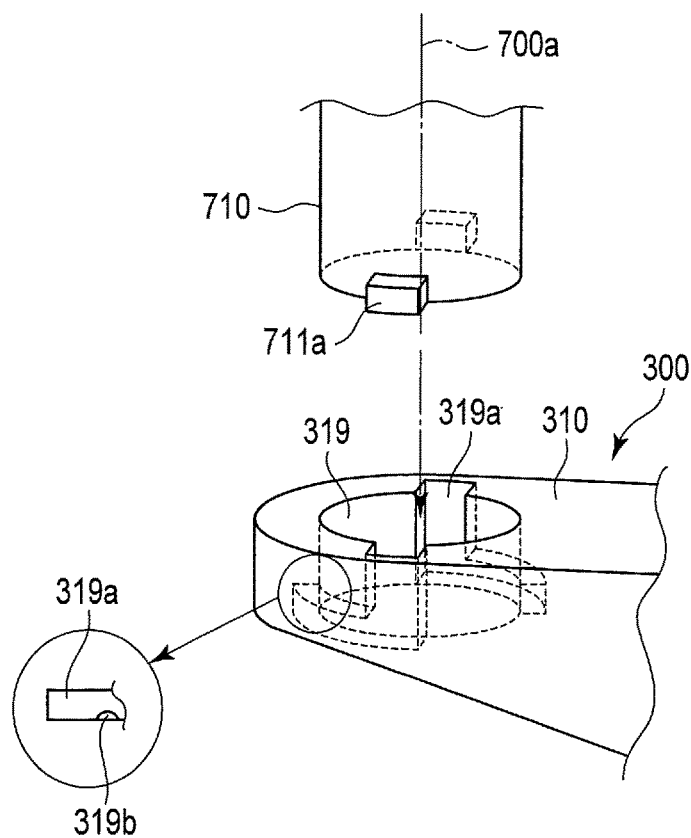
F I G. 8A
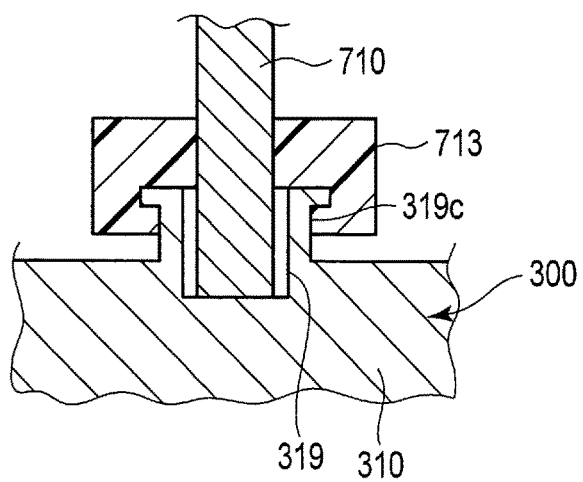
F I G. 8B

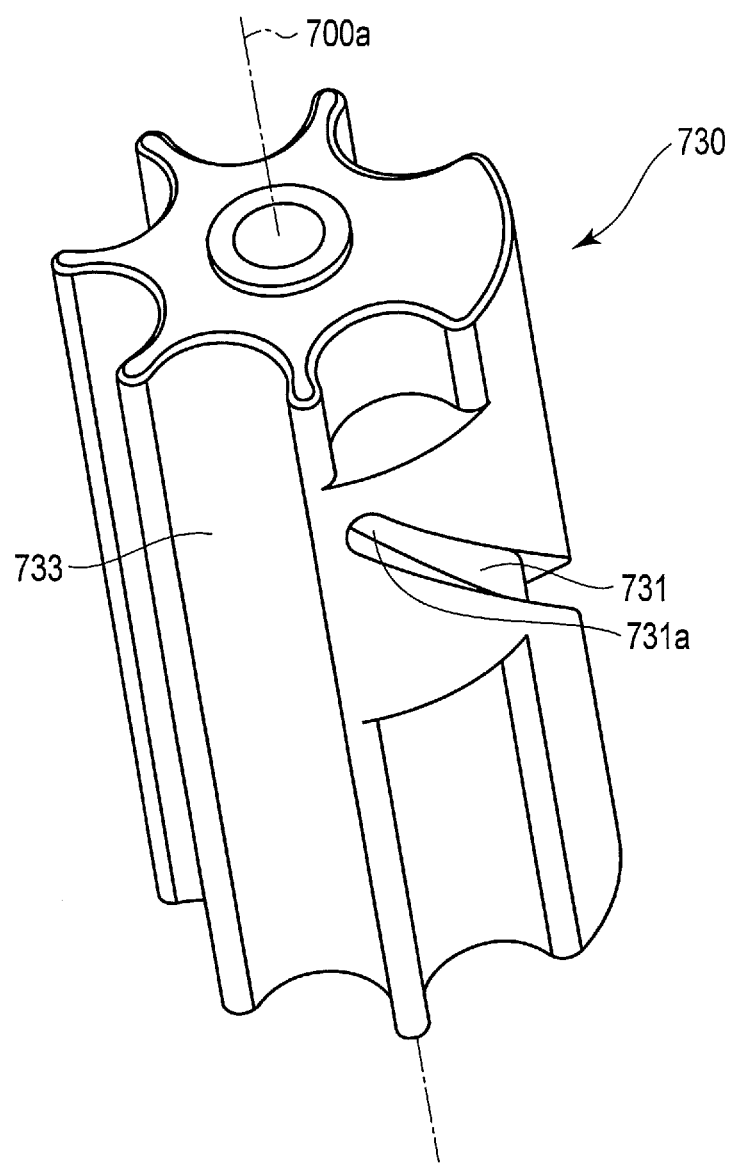
F I G. 9A

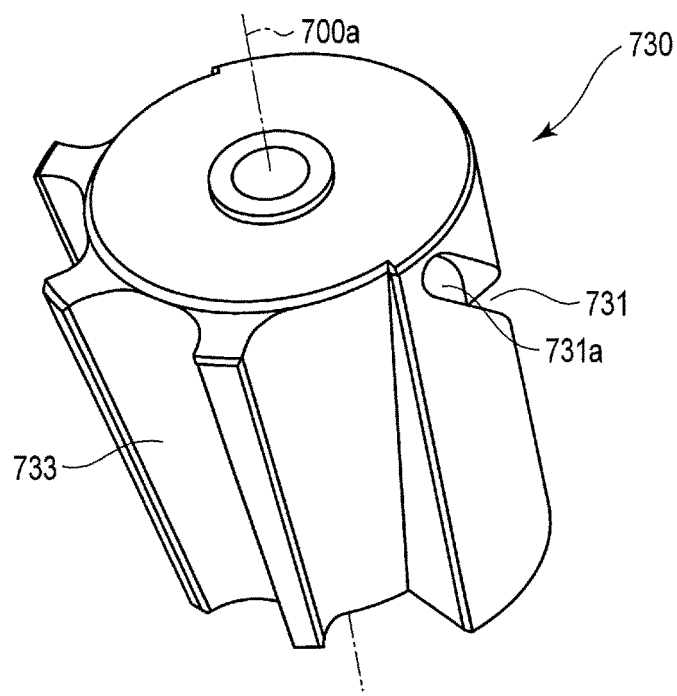
F I G. 9D
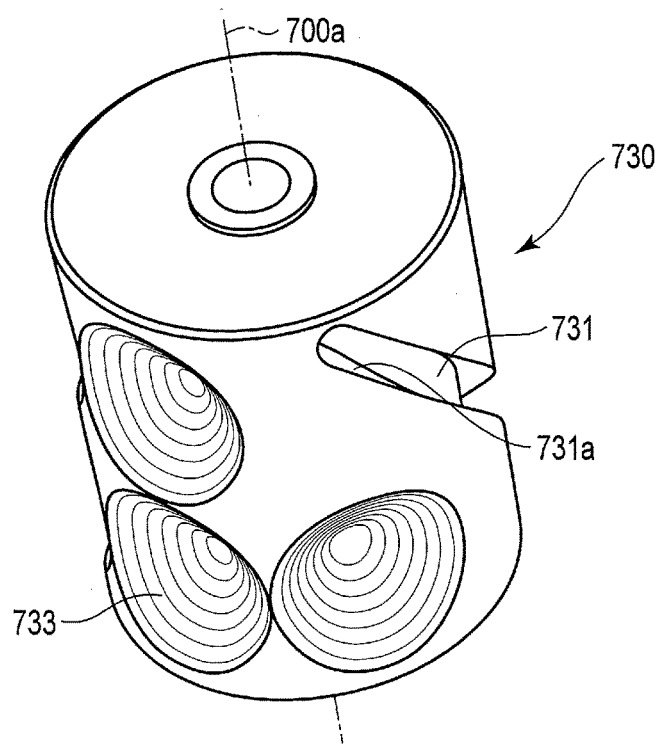
F I G. 9E

ADVANCE AND RETREAT ASSIST TOOL FOR ENDOSCOPIC TREATMENT INSTRUMENT

CROSS-REFERENCE TO RELATED APPLICATIONS

This application is a Continuation application of PCT Application No. PCT/JP2014/050023, filed Jan. 6, 2014 and based upon and claiming the benefit of priority from prior Japanese Patent Application No. 2013-037223, filed Feb. 27, 2013, the entire contents of all of which are incorporated herein by reference.

BACKGROUND OF THE INVENTION

1. Field of the Invention

The present invention relates to an advance and retreat assist tool for an endoscopic treatment instrument.

2. Description of the Related Art

For example, Jpn. Pat. Appln. KOKAI Publication No. 2008-080119, Jpn. Pat. Appln. KOKAI Publication No. 2003-265406, Japanese Registered Utility Model Publication No. 2560353, and Jpn. Pat. Appln. KOKAI Publication No. 9-276211 have each disclosed an advance and retreat assist tool for an endoscopic treatment instrument which assists a treatment instrument of an endoscope in advancing and retreating.

For example, in Jpn. Pat. Appln. KOKAI Publication No. 2008-080119, Jpn. Pat. Appln. KOKAI Publication No. 2003-265406, Japanese Registered Utility Model Publication No. 2560353, and Jpn. Pat. Appln. KOKAI Publication No. 9-276211, the advance and retreat assist tool is attached to a treatment instrument insertion hole portion so that the advance and retreat assist tool is provided straight along the central axis direction of the treatment instrument insertion hole portion provided in a treatment instrument insertion portion. The central axis direction of the treatment instrument insertion hole portion is slanted relative to the central axis direction of a grasping portion. Thus, the advance and retreat assist tool is slanted relative to the central axis direction of the grasping portion.

BRIEF SUMMARY OF THE INVENTION

An aspect of an advance and retreat assist tool for an endoscopic treatment instrument includes a base unit including a hole portion through which the endoscopic treatment instrument to be inserted into an endoscope passes; an attachment portion which attaches the base unit to a treatment instrument insertion portion of the endoscope so that the hole portion faces a treatment instrument insertion hole portion provided in the treatment instrument insertion portion; a tubular member provided to advance and retreat relative to the base unit coaxially with a central axis of the hole portion; a fixing portion which fixes the endoscopic treatment instrument to the tubular member; a rotary portion which has an axis different from an axis of the tubular member and which rotates around the axis; and an advance and retreat mechanism provided in the rotary portion and the tubular member, the advance and retreat mechanism converting a rotation force of the rotary portion during the rotation of the rotary portion to an advance and retreat force to advance and retreat the tubular member in the axial direction of the tubular member, the advance and retreat mechanism transmitting the advance and retreat force to the tubular member and thereby advancing and retreating the tubular member.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a schematic diagram showing how an advance and retreat assist tool according to a first embodiment of the present invention is attached to an endoscope and how a treatment instrument advances;

FIG. 1B is a schematic diagram showing how the advance and retreat assist tool is attached to the endoscope and how the treatment instrument retreats;

FIG. 4A is a sectional view of an advance and retreat unit during the advance of the treatment instrument;

FIG. 4B is a sectional view of the advance and retreat unit during the retreat of the treatment instrument;

FIG. 5C is a schematic diagram showing the positional relation between the grasping portion, the outer cylindrical portion, the clearance, and the rotary portion;

FIG. 6A is a diagram showing a modification of a rotation prevention portion;

FIG. 6B is a diagram showing the modification of the rotation prevention portion;

FIG. 7E is a diagram showing how a cam member is engaged with an edge of a groove portion;

FIG. 7F is a diagram showing how the cam member is disengaged with the edge of the groove portion;

FIG. 8A is a diagram showing a first modification of the attachment of a rotation shaft member to the base member;

FIG. 8B is a diagram showing a second modification of the attachment of the rotation shaft member to the base member;

FIG. 9A is a diagram showing a first modification of the rotation body member;

FIG. 9D is a diagram showing a fourth modification of the rotation body member; and FIG. 9E is a diagram showing a fifth modification of the rotation body member.

DETAILED DESCRIPTION OF THE INVENTION

Hereinafter, embodiments of the present invention will be described in detail with reference to the drawings.

[First Embodiment]

[Configuration]

The first embodiment is described with reference to FIG. 1A, FIG. 1B, FIG. 1C, FIG. 2A, FIG. 2B, FIG. 2C, FIG. 2D, FIG. 2E, FIG. 3A, FIG. 3B, FIG. 4A, FIG. 4B, FIG. 5A, FIG. 5B, and FIG. 5C. Some components are not shown for clarity in some of the drawings.

Figure 3A:
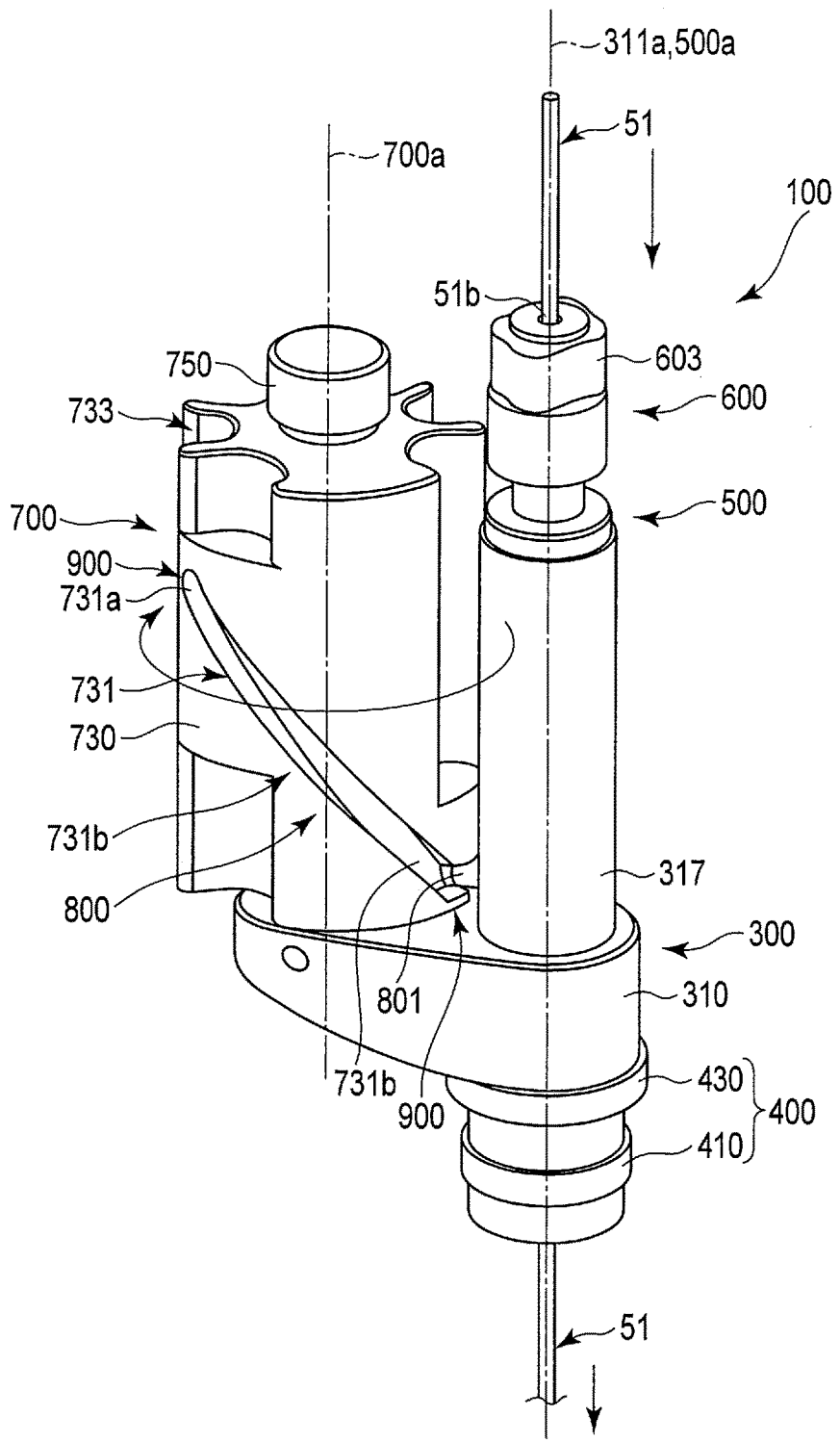
FIG. 3A is a perspective view of the advance and retreat assist tool during the advance of the treatment instrument.

As shown in FIG. 1A, FIG. 3A, and FIG. 4A, the advance of a first tubular member 500 means that the first tubular member 500 moves along the direction of a second central axis 500a so that the first tubular member 500 is inserted into an outer cylindrical portion 317.

Figure 3B:
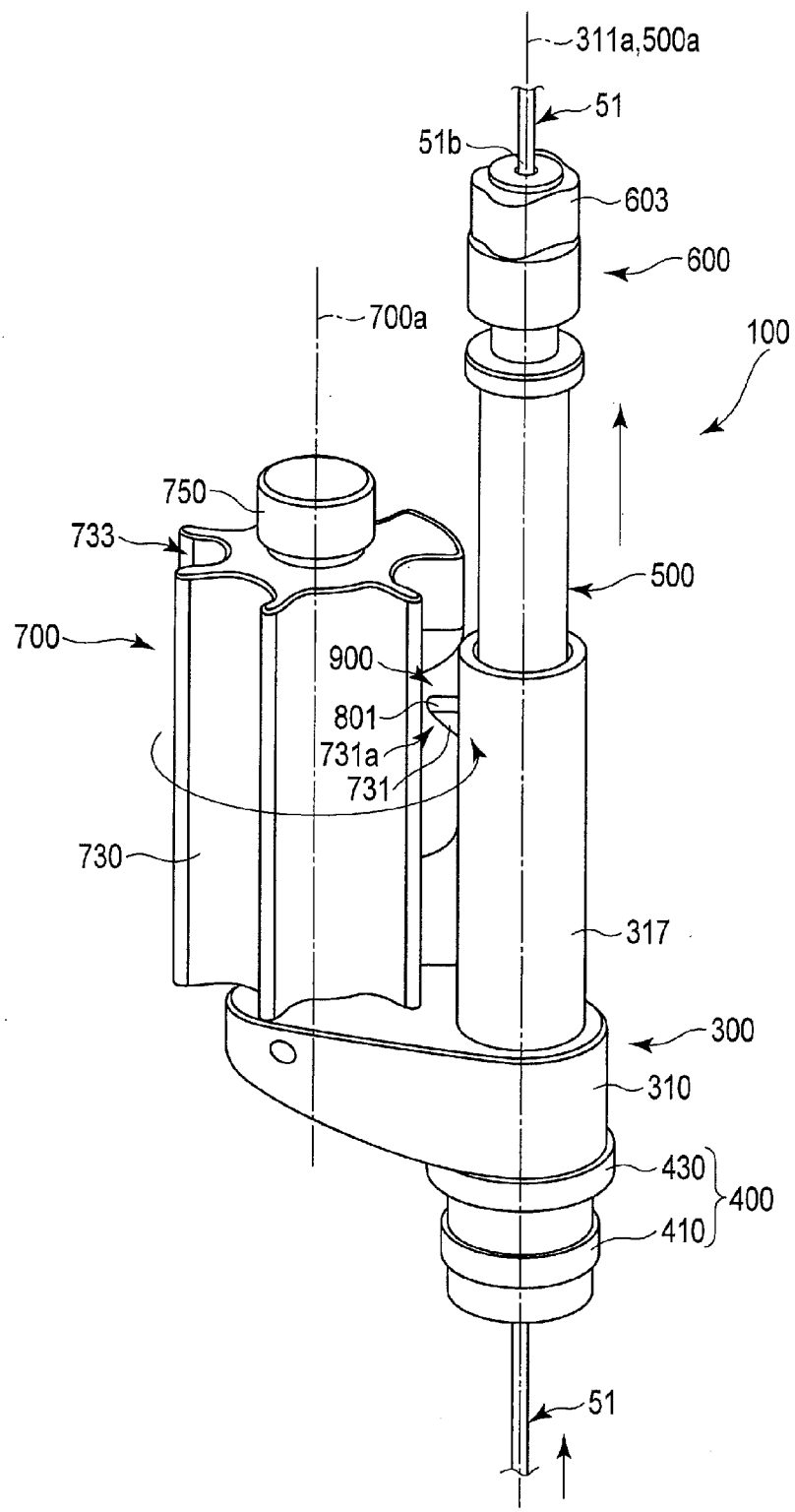
FIG. 3B is a perspective view of the advance and retreat assist tool during the retreat of the treatment instrument.

As shown in FIG. 1B, FIG. 3B, and FIG. 4B, the retreat of the first tubular member 500 means that the first tubular member 500 moves along the direction of the second central axis 500a so that the first tubular member 500 is removed from the outer cylindrical portion 317.

As shown in FIG. 1A, FIG. 1B, FIG. 3A, FIG. 3B, FIG. 4A, and FIG. 4B, for example, the advance and retreat of the first tubular member 500 include the advance of the first tubular member 500 and the retreat of the first tubular member 500.

As shown in FIG. 1A, FIG. 3A, and FIG. 4A, for example, the advance of a treatment instrument 51 means that the treatment instrument 51 moves so that the treatment instrument 51 moves to the side of a distal end hard portion 21 from the side of an operation portion 30 and a distal end portion 51a of the treatment instrument 51 projects outward from the inside of an insertion portion 20 via a distal opening portion 35b in response to the advance of the first tubular member 500.

As shown in FIG. 1B, FIG. 3B, and FIG. 4B, for example, the retreat of the treatment instrument 51 means that the treatment instrument 51 moves so that the treatment instrument 51 moves to the side of the operation portion 30 from the side of the distal end hard portion 21 and the distal end portion 51a of the treatment instrument 51 is housed in the insertion portion 20 from the outside via the distal opening portion 35b in response to the retreat of the first tubular member 500.

As shown in FIG. 1A, FIG. 1B, FIG. 3A, FIG. 3B, FIG. 4A, and FIG. 4B, for example, the advance and retreat of the treatment instrument 51 include the advance of the treatment instrument 51 and the retreat of the treatment instrument 51.

[Endoscopic System 5]

As shown in FIG. 1A and FIG. 1B, an endoscopic system has an endoscope 10, the endoscopic treatment instrument (hereinafter, treatment instrument 51), and an advance and retreat assist tool 100 for the treatment instrument 51.

[Endoscope 10]

The endoscope 10 has a hollow and elongated insertion portion 20 to be inserted into, for example, a body cavity, and the operation portion 30 which is coupled to a proximal end portion of the insertion portion 20 and which operates the endoscope 10.

[Insertion Portion 20]

The insertion portion 20 has the distal end hard portion 21, a bending portion 23, and a flexible tubular portion 25 from the distal end portion side of the insertion portion 20 to the proximal end portion side of the insertion portion 20. A proximal end portion of the distal end hard portion 21 is coupled to a distal end portion of the bending portion 23, and a proximal end portion of the bending portion 23 is coupled to a distal end portion of the flexible tubular portion 25.

The distal end hard portion 21 is the distal end portion of the insertion portion 20, and is hard and unbendable. The distal end hard portion 21 has the distal opening portion 35b, and an unshown observation window included in an unshown observation optical system. The distal end hard portion 21 also has an unshown pair of illumination windows which are provided across the observation window and which are included in an unshown illumination optical system, and a nozzle which supplies gas and water to the observation window. The distal opening portion 35b, the observation window, the illumination windows, and the nozzle are provided in a distal end face of the distal end hard portion 21.

The bending portion 23 is bent in a desired direction, for example, in an upward, downward, leftward, or rightward direction by the operation of a later-described bending operation portion 37. When the bending portion 23 is bent, the position and direction of the distal end hard portion 21 are changed. An observation target is illuminated by unshown illumination light, and the observation target enters into an observation field. This observation target is, for example, an affected part or a lesion in a subject (e.g., body cavity).

The flexible tubular portion 25 has desired flexibility. Therefore, the flexible tubular portion 25 is bent by an external force. The flexible tubular portion 25 is a tubular member extending from a later-described body portion 31 in the operation portion 30.

[Operation Portion 30]

The operation portion 30 has the body portion 31 from which the flexible tubular portion 25 extends, a grasping portion 33 which is coupled to the proximal end portion of the body portion 31 and which is grasped by a surgeon who operates the endoscope 10, and a universal cord 41 connected to the grasping portion 33.

[Grasping Portion 33]

Figure 5A:
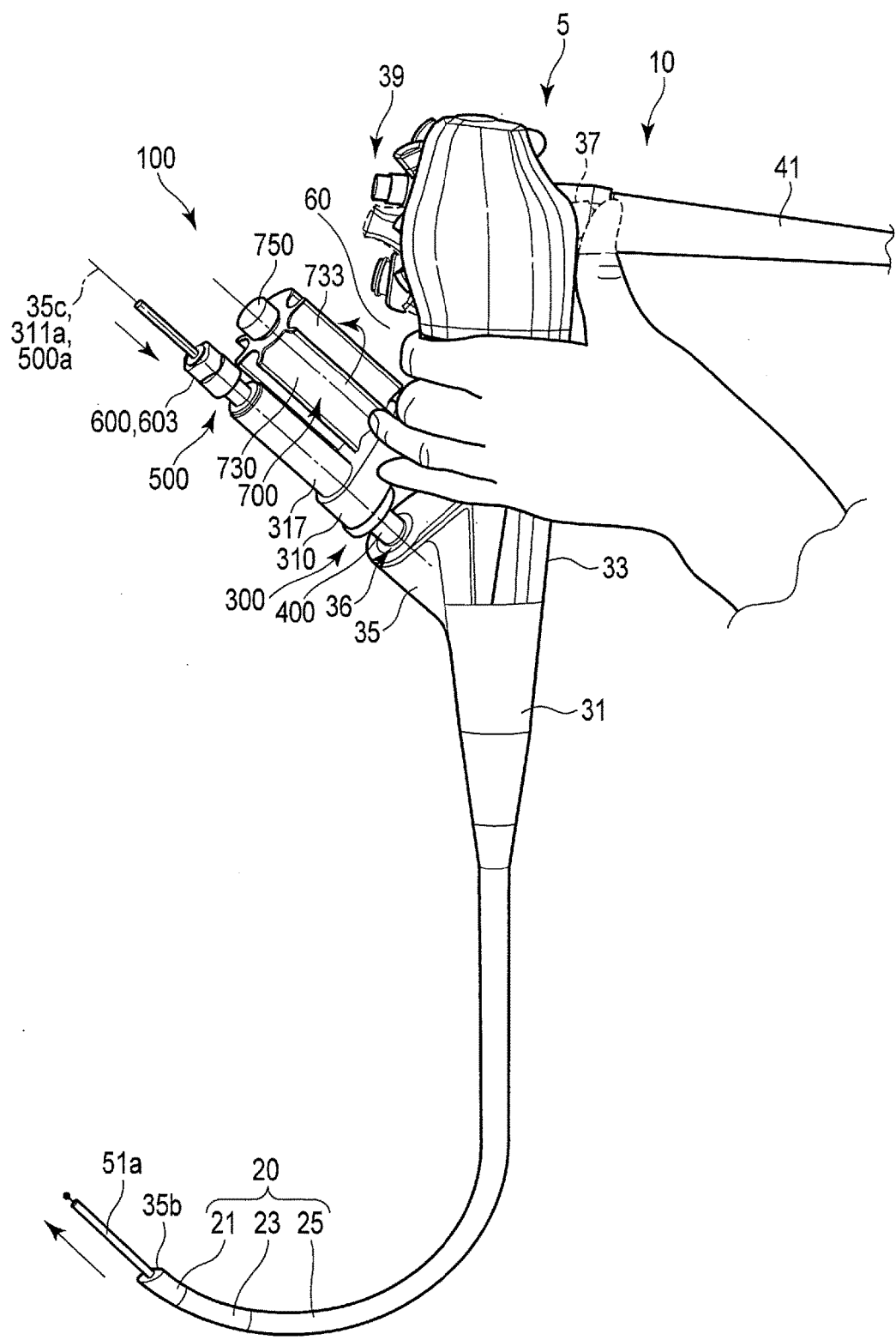
FIG. 5A is a schematic diagram showing how the rotary portion is provided inside a clearance, a grasping portion is grasped by the left hand of a surgeon, a bending operation portion and the rotary portion are operated by the fingers of the left hand, and the endoscope is grasped and the treatment instrument is advanced and retreated with one hand at the same time, in the endoscope to which the advance and retreat assist tool is attached.

The grasping portion 33 has a treatment instrument insertion portion 35, the bending operation portion 37 which is operated to bend the bending portion 23, and a switch portion 39. The treatment instrument insertion portion 35 is provided on the distal end portion side of the grasping portion 33. The bending operation portion 37 and the switch portion 39 are provided on the proximal end portion side of the grasping portion 33. As shown in FIG. 5A, the grasping portion 33 is grasped by the left hand of the surgeon, and the bending operation portion 37 and the switch portion 39 are operated by the fingers of the left hand.

[Treatment Instrument Insertion Portion 35]

The treatment instrument insertion portion 35 branches off from the grasping portion 33. Thus, as shown in FIG. 1A and FIG. 1B, the central axis direction of the treatment instrument insertion portion 35 is slanted relative to the direction of a central axis 33a of the grasping portion 33.

As shown in FIG. 1A and FIG. 1B, the treatment instrument insertion portion 35 has a treatment instrument insertion hole portion 35a which is provided at the end portion of the treatment instrument insertion portion 35 and which is used to insert the treatment instrument 51 into the endoscope 10.

The treatment instrument insertion hole portion 35a is coupled to a proximal end portion of an unshown treatment instrument insertion channel. The treatment instrument insertion channel is provided inside the insertion portion 20, and provided from the flexible tubular portion 25 to the distal end hard portion 21 via the bending portion 23. A distal end portion of the treatment instrument insertion channel is in communication with the distal opening portion 35b provided in the distal end hard portion 21. The treatment instrument insertion hole portion 35a is an insertion hole portion used to insert the treatment instrument 51 into the treatment instrument insertion channel.

As shown in FIG. 1A and FIG. 1B, a central axis 35c of the treatment instrument insertion hole portion 35a is provided coaxially with the central axis of the treatment instrument insertion portion 35, and is thus slanted relative to the central axis 33a of the grasping portion 33. The direction of the central axis 35c is slanted relative to the direction of the central axis 33a of the grasping portion 33.

As shown in FIG. 1A, FIG. 1B, FIG. 2C, FIG. 4A, FIG. 4B, FIG. 5A, and FIG. 5B, the treatment instrument insertion portion 35 further has a cylindrical treatment instrument insertion cap 36 to be inserted into the treatment instrument insertion hole portion 35a. The treatment instrument insertion cap 36 is made of, for example, a metal. The central axis of the treatment instrument insertion cap 36 is provided coaxially with the central axis 35c of the treatment instrument insertion hole portion 35a. Thus, the treatment instrument insertion cap 36 is slanted relative to the grasping portion 33. When the cylindrical treatment instrument insertion cap 36 is inserted in the treatment instrument insertion hole portion 35a, the treatment instrument insertion cap 36 is in communication with the treatment instrument insertion channel.

The treatment instrument 51 is inserted into the treatment instrument insertion channel from the treatment instrument insertion hole portion 35a via the treatment instrument insertion cap 36, and pressed to the side of the distal end hard portion 21. As shown in FIG. 1A and FIG. 1B, the treatment instrument 51 is then projected from the distal opening portion 35b.

As shown in FIG. 1A, FIG. 1B, FIG. 2A, FIG. 2C, FIG. 4A, FIG. 4B, FIG. 5A, and FIG. 5B, the advance and retreat assist tool 100 is attached to the treatment instrument insertion cap 36. In this case, the treatment instrument insertion cap 36 is brought into communication with a first hole portion 311 of a later-described base member 310.

Figure 2A:
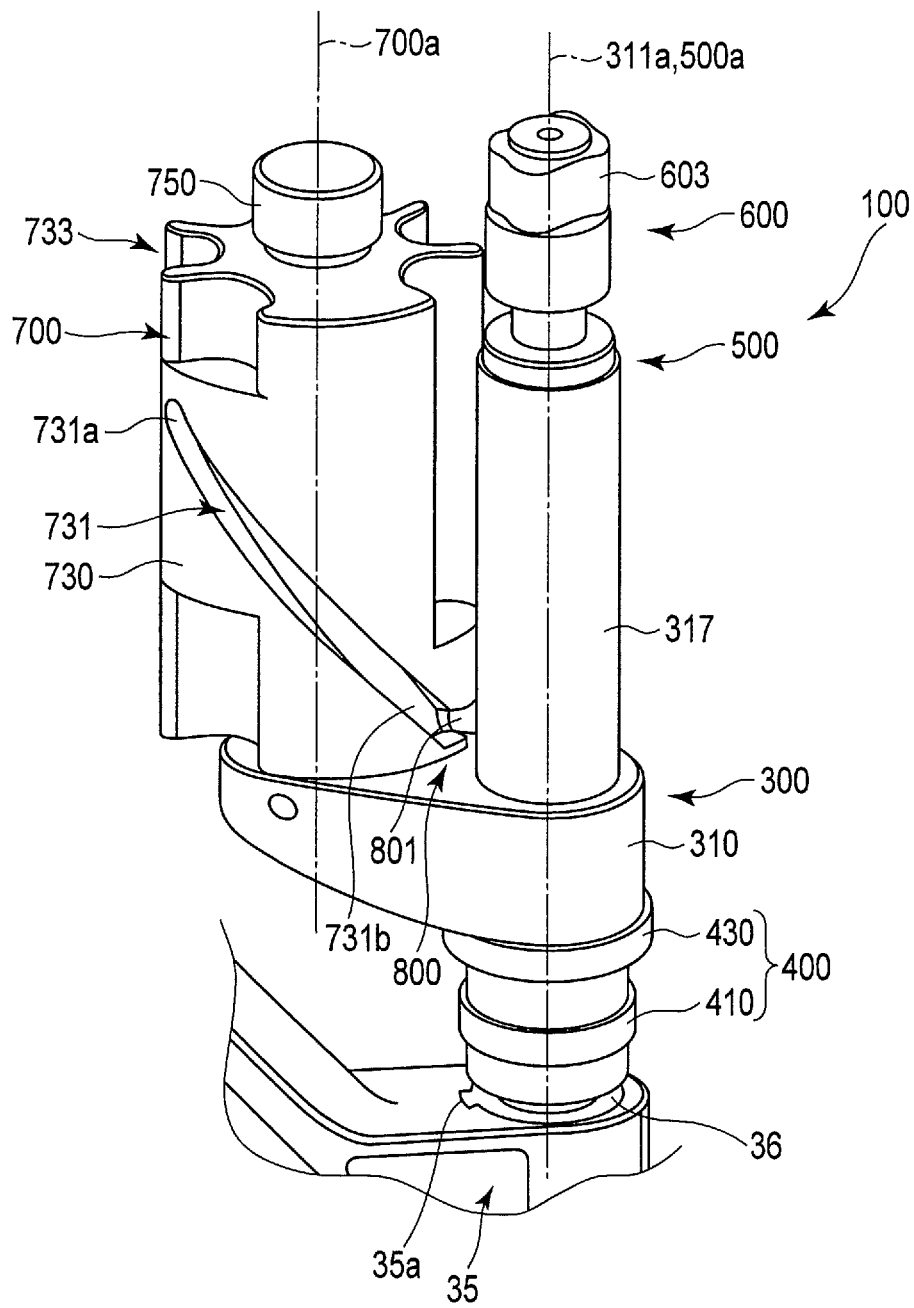
FIG. 2A is a perspective view of the advance and retreat assist tool.
Figure 2B:
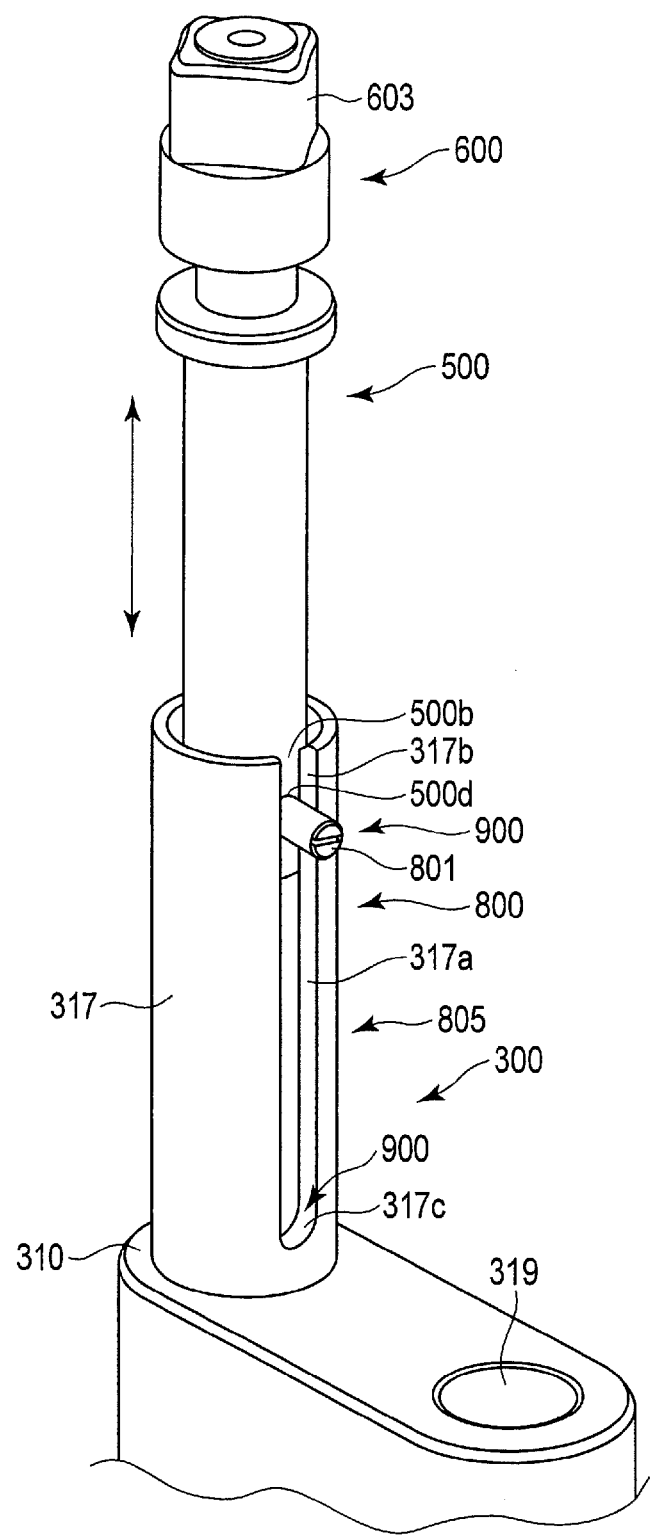
FIG. 2B is a perspective view of a base member including an outer cylindrical portion and a recess portion on which a first tubular member slides.
Figure 2C:
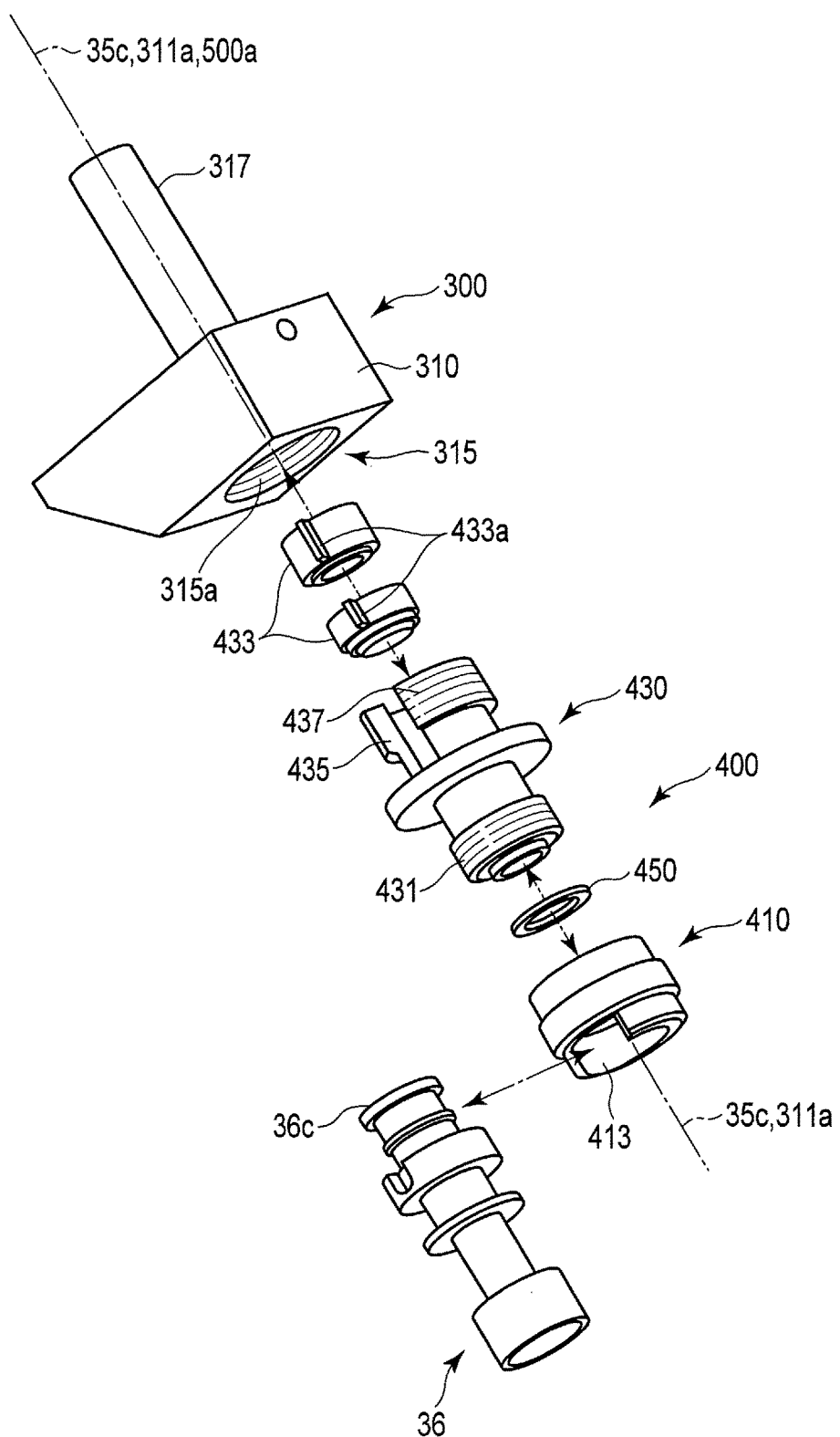
FIG. 2C is an exploded perspective view of an attachment portion, and is a diagram illustrating the attachment of a body portion and a support portion, the attachment of the body portion to a treatment instrument insertion cap, and the attachment of the support portion to the base member.

As shown in FIG. 2C, FIG. 4A, and FIG. 4B, the treatment instrument insertion cap 36 has a distal end portion to be inserted into the treatment instrument insertion hole portion 35a, and a proximal end portion which projects outside the treatment instrument insertion hole portion 35a and which is exposed to the outside. The proximal end portion has an edge portion 36c. The edge portion 36c is formed as an outer flange, and is folded outward in the diametrical direction of the treatment instrument insertion cap 36.

[Bending Operation Portion 37]

The bending operation portion 37 has a horizontal bending operation knob 37a which is operated to horizontally bend the bending portion 23, a vertical bending operation knob 37b which is operated to vertically bend the bending portion 23, and a fixing knob 37c which fixes the position of the bent bending portion 23.

[Switch Portion 39]

The switch portion 39 is operated by the hand of the surgeon when the grasping portion 33 is grasped by the surgeon. The switch portion 39 is operated during the operation of various functions of the endoscope such as gas supply, water supply, suction, and photography.

[Universal Cord 41]

The universal cord 41 has an unshown connector which can be attached to and removed from an unshown control apparatus.

[Treatment Instrument 51]

The treatment instrument 51 is formed by, for example, an elongated linear member.

[Advance and Retreat Assist Tool 100]

Figure 1C:
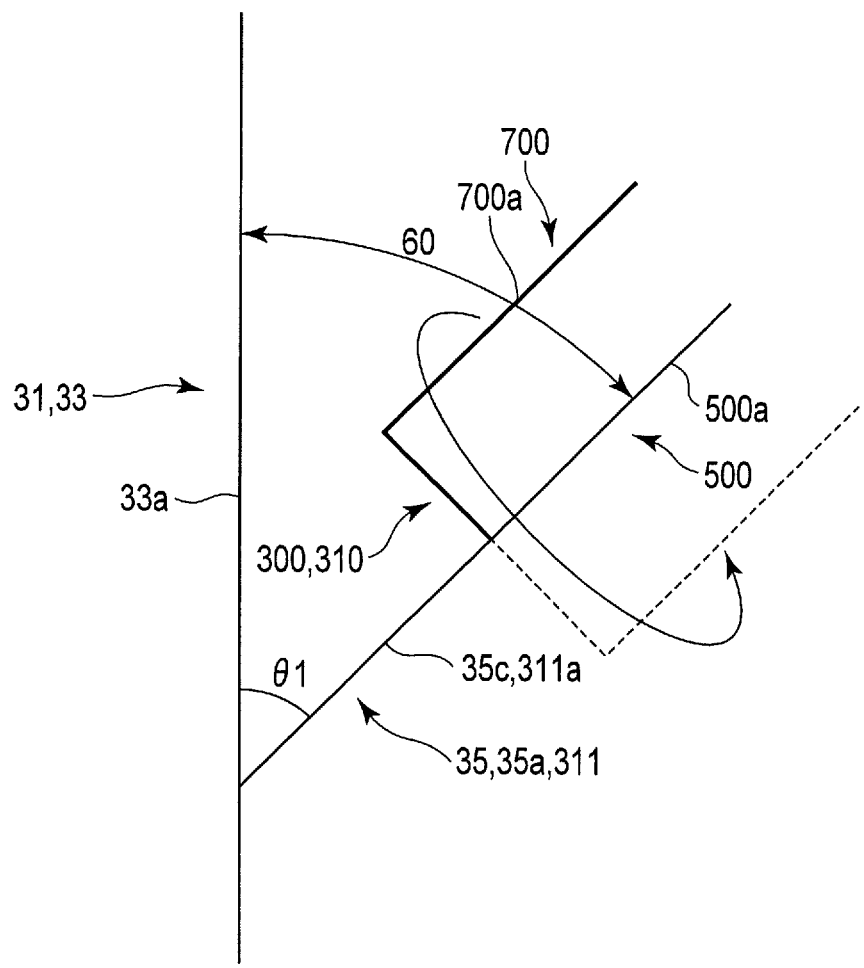
FIG. 1C is a diagram showing an angle θ1, and a rotary portion which rotates around a rotation central axis.

As shown in FIG. 1A and FIG. 1B, the advance and retreat assist tool 100 is removably attached to the endoscope 10, in particular, the treatment instrument insertion portion 35. More specifically, the advance and retreat assist tool 100 is removably attached to the treatment instrument insertion cap 36 which is inserted into the treatment instrument insertion hole portion 35a of the treatment instrument insertion portion 35 so that the advance and retreat assist tool 100 is rotatable around the central axis of the treatment instrument insertion cap 36 (the central axis 35c of the treatment instrument insertion hole portion 35a) as shown in FIG. 1C, FIG. 5A, FIG. 5B, and FIG. 5C. The advance and retreat assist tool 100 assists the treatment instrument 51 in advancing and retreating along the longitudinal axis direction of the treatment instrument 51. The treatment instrument 51 is inserted into the endoscope 10 from the treatment instrument insertion hole portion 35a via the treatment instrument insertion cap 36. The distal end portion 51a of the treatment instrument 51 can project from the distal opening portion 35b.

As shown in FIG. 1A FIG. 1B, FIG. 1C, FIG. 5A, FIG. 5B, and FIG. 5C, the advance and retreat assist tool 100 has a base unit 300, and an attachment portion 400 which removably attaches the base unit 300 to the treatment instrument insertion portion 35 (the treatment instrument insertion cap 36) so that the base unit 300 is rotatable around the central axis 35c of the treatment instrument insertion hole portion 35a (the treatment instrument insertion cap 36). As shown in FIG. 1A FIG. 1B, FIG. 5A, and FIG. 5B, the advance and retreat assist tool 100 further has the first tubular member 500 through which the treatment instrument 51 is inserted and which guides the treatment instrument 51 to the endoscope 10 via the base unit 300, and a fixing portion 600 which fixes the treatment instrument 51 to the first tubular member 500. As shown in FIG. 1A, FIG. 1B, FIG. 2A, FIG. 2D, FIG. 2E, FIG. 3A, FIG. 3B, FIG. 4A, FIG. 4B, FIG. 5A, FIG. 5B, and FIG. 5C, the advance and retreat assist tool 100 further has a rotary portion 700 removably provided in the base unit 300 adjacent to the first tubular member 500, an advance and retreat mechanism 800 which advances and retreats the first tubular member 500 by a rotation force of the rotary portion 700, and a regulating mechanism 900 which regulates the advance and retreat of the first tubular member 500.

[Base Unit 300]

As shown in FIG. 1A, FIG. 1B, FIG. 1C, FIG. 3A, FIG. 3B, FIG. 4A, FIG. 4B, FIG. 5A, FIG. 5B, and FIG. 5C, the base unit 300 is removably attached to the treatment instrument insertion cap 36 by the attachment portion 400. The base unit 300 is also attached to the treatment instrument insertion cap 36 by the attachment portion 400 rotatably around the central axis of the treatment instrument insertion cap 36. As shown in FIG. 2A and FIG. 2B, the base unit 300 has the base member 310.

As shown in FIG. 1A and FIG. 1B, the base member 310 is provided to face the treatment instrument insertion hole portion 35a in the direction of the central axis 35c of the treatment instrument insertion hole portion 35a when the advance and retreat assist tool 100 is attached to the endoscope 10.

[Base Member 310]

As shown in FIG. 4A and FIG. 4B, the base member 310 has the first hole portion 311 having a first central axis 311a.

The first hole portion 311 faces the inside of the treatment instrument insertion cap 36 and the treatment instrument insertion channel when the advance and retreat assist tool 100 is attached to the endoscope 10. At the same time, as shown in FIG. 1A, FIG. 1B, and FIG. 1C, the first central axis 311a of the first hole portion 311 is provided coaxially with the central axis 35c of the treatment instrument insertion hole portion 35a, and is slanted relative to the central axis 33a of the grasping portion 33.

The first hole portion 311 is in communication with the outside in one end face of the base member 310. The first hole portion 311 is depressed in one end face of the base member 310.

As shown in FIG. 4A and FIG. 4B, the first hole portion 311 functions as a guide hole portion which guides, to the treatment instrument insertion hole portion 35a via the attachment portion 400 and the treatment instrument insertion cap 36, the treatment instrument 51 through which the first tubular member 500 is inserted. The second hole portion 313 has substantially the same diameter as that of the treatment instrument 51.

As shown in FIG. 2C, FIG. 4A, and FIG. 4B, the base member 310 further has a second hole portion 315 which is in communication with the first hole portion 311 and which is larger than the first hole portion 311. A central axis of the second hole portion 315 is provided coaxially with the first central axis 311a of the first hole portion 311.

The second hole portion 315 is in communication with the outside in the other end face of the base member 310, and is depressed in the other end face of the base member 310. The second hole portion 315 is provided on the side of the treatment instrument insertion cap 36. A support portion 430 of the attachment portion 400 is screwed into the second hole portion 315.

As shown in FIG. 1A, FIG. 1B, FIG. 2B, FIG. 3A, FIG. 3B, FIG. 4A, FIG. 4B, FIG. 5A, and FIG. 5B, the base member 310 further has the outer cylindrical portion 317 which is erected relative to the base member 310 integrally with the base member 310 and through which the first tubular member 500 is inserted. The outer cylindrical portion 317 has, for example, a circular cylindrical shape. The outer cylindrical portion 317 is in communication with the first hole portion 311, and is provided around the first hole portion 311. A central axis of the outer cylindrical portion 317 is provided coaxially with the first central axis 311a of the first hole portion 311. The inside diameter of the outer cylindrical portion 317 is larger than the diameter of the first hole portion 311.

As shown in FIG. 1A, FIG. 1B, FIG. 2B, FIG. 3A, FIG. 3B, FIG. 4A, and FIG. 4B, the first tubular member 500 slides on the outer cylindrical portion 317 along the first central axis 311a of the first hole portion 311 to advance and retreat the outer cylindrical portion 317. The outer cylindrical portion 317 is shorter than the first tubular member 500. The outer cylindrical portion 317 may be independent of the base member 310. In this case, how to attach the outer cylindrical portion 317 to the base member 310 is not particularly limited; for example, a distal end portion 317c of the outer cylindrical portion 317 is removably fitted into the first hole portion 311.

As shown in FIG. 2B, the outer cylindrical portion 317 holds the first tubular member 500 so that the second central axis 500a of the first tubular member 500 is provided coaxially with the first central axis 311a and so that the first tubular member 500 advances and retreats along the second central axis 500a of the first tubular member 500, whereby the movement of the first tubular member 500 in a direction that intersects at right angles with the direction of the second central axis 500a is prevented, and the shaking of the first tubular member 500 is prevented. Thus, the outside diameter of the first tubular member 500 is substantially the same as the inside diameter of the outer cylindrical portion 317.

As shown in FIG. 2B, the outer cylindrical portion 317 has a long opening portion 317a which is provided in the outer cylindrical portion 317 along the direction of the first central axis 311a (the second central axis 500a), a later-described protrusion portion 801 passes through the long opening portion 317a in the diametrical direction of the outer cylindrical portion 317, and the protrusion portion 801 slides in the long opening portion 317a along the direction of the first central axis 311a (the second central axis 500a). A proximal end portion 317b of the long opening portion 317a is open so that the protrusion portion 801 is inserted into the long opening portion 317a.

As shown in FIG. 2B, FIG. 4A, and FIG. 4B, the base member 310 has a depression portion 319 which is depressed in one end face of the base member 310 and which is provided on the side of the first hole portion 311 adjacent to the first hole portion 311. Thus, a central axis of the depression portion 319 is provided parallel to the first central axis 311a in a direction that intersects at right angles with the direction of the first central axis 311a. This depression portion 319 is provided apart from the first hole portion 311 and the outer cylindrical portion 317 in the direction that intersects at right angles with the direction of the first central axis 311a so that a later-described rotation body member 730 can rotate around a third central axis 700a.

[Attachment Portion 400]

As shown in FIG. 1A, FIG. 1B, FIG. 4A, FIG. 4B, FIG. 5A, FIG. 5B, and FIG. 5C, the attachment portion 400 removably attaches the base unit 300 to the treatment instrument insertion portion 35 (the treatment instrument insertion cap 36) so that the first central axis 311a is provided coaxially with the central axis 35c of the treatment instrument insertion hole portion 35a, so that the first hole portion 311 faces the treatment instrument insertion hole portion 35a, and so that the base member 310 of the base unit 300 is rotatable around the central axis 35c of the treatment instrument insertion hole portion 35a (the central axis of the treatment instrument insertion cap 36).

As shown in FIG. 2C, FIG. 4A, FIG. 4B, FIG. 5A, FIG. 5B, and FIG. 5C, the attachment portion 400 has a cylindrical body portion 410 which is removably attached to the treatment instrument insertion cap 36 so that the body portion 410 is rotatable around the central axis 35c of the treatment instrument insertion hole portion 35a, and the cylindrical support portion 430 which is removably attached to the body portion 410 and which supports the base member 310. The body portion 410 is independent of the support portion 430. The body portion 410 and the support portion 430 are provided by an elastic material such as a resin or rubber.

[Attachment of Body Portion 410 and Support Portion 430]

As shown in FIG. 4A and FIG. 4B, the body portion 410 has a body thread groove portion 411 formed in the inner circumferential surface of the body portion 410. The body thread groove portion 411 is provided at a proximal end portion of the body portion 410.

As shown in FIG. 2C, FIG. 4A, and FIG. 4B, the support portion 430 has a distal support thread groove portion 431 which is formed in the outer circumferential surface of the support portion 430 and which meshes with the body thread groove portion 411. The distal support thread groove portion 431 is provided at a distal end portion of the support portion 430.

The support portion 430 is attached to the body portion 410 when the support portion 430 is screwed into the body portion 410 in the central axis direction of the attachment portion 400 as shown in FIG. 2C so that the body thread groove portion 411 and the distal support thread groove portion 431 mesh with each other while the body portion 410 is attached to the treatment instrument insertion cap 36. Thus, the body portion 410 and the support portion 430 are fastened to each other. At the same time, the body portion 410 and the support portion 430 communicate with the treatment instrument insertion cap 36.

As shown in FIG. 4A, and FIG. 4B, when the support portion 430 is attached to the body portion 410, the edge portion 36c of the treatment instrument insertion cap 36 formed as the outer flange is provided between the support portion 430 and a distal end portion of the body portion 410 formed as an inner flange in the direction of the central axis 35c of the treatment instrument insertion hole portion 35a. The support portion 430 is attached to the body portion 410 so that the support portion 430 presses the edge portion 36c into the distal end portion of the body portion 410. Thus, the attachment portion 400 is fixed to the treatment instrument insertion cap 36.

As shown in FIG. 2C, FIG. 4A, and FIG. 4B, the advance and retreat assist tool 100 further has an interference prevention member 450 which intervenes between the support portion 430 and the edge portion 36c of the treatment instrument insertion cap 36 in the direction of the central axis 35c of the treatment instrument insertion hole portion 35a and which prevents interference between the support portion 430 and the edge portion 36c. The interference prevention member 450 is made of, for example, PTFE. The interference prevention member 450 is in close contact with the support portion 430 and the edge portion 36c of the treatment instrument insertion cap 36.

[Body Portion 410]

As shown in FIG. 2C, the body portion 410 has a cutout portion 413 which is formed by the depression of a part of the edge portion of the body portion 410 in the central axis direction of the body portion 410. The cutout portion 413 is provided at the distal end portion of the body portion 410. The cutout portion 413 is not provided flush with the body thread groove portion 411, and is provided closer to the side of the treatment instrument insertion hole portion 35a to the body thread groove portion 411. The cutout portion 413 is not formed over the entire circumference of the body portion 410 in the circumferential direction of the body portion 410, but is formed in a size smaller than, for example, a semicircle. This cutout portion 413 is in communication with the inside of body portion 410 in the diametrical direction of the body portion 410.

As described above, the distal end portion of the body portion 410 is folded inward as the inner flange.

[Attachment of Body Portion 410 to Treatment Instrument Insertion Cap 36]

Figure 5B:
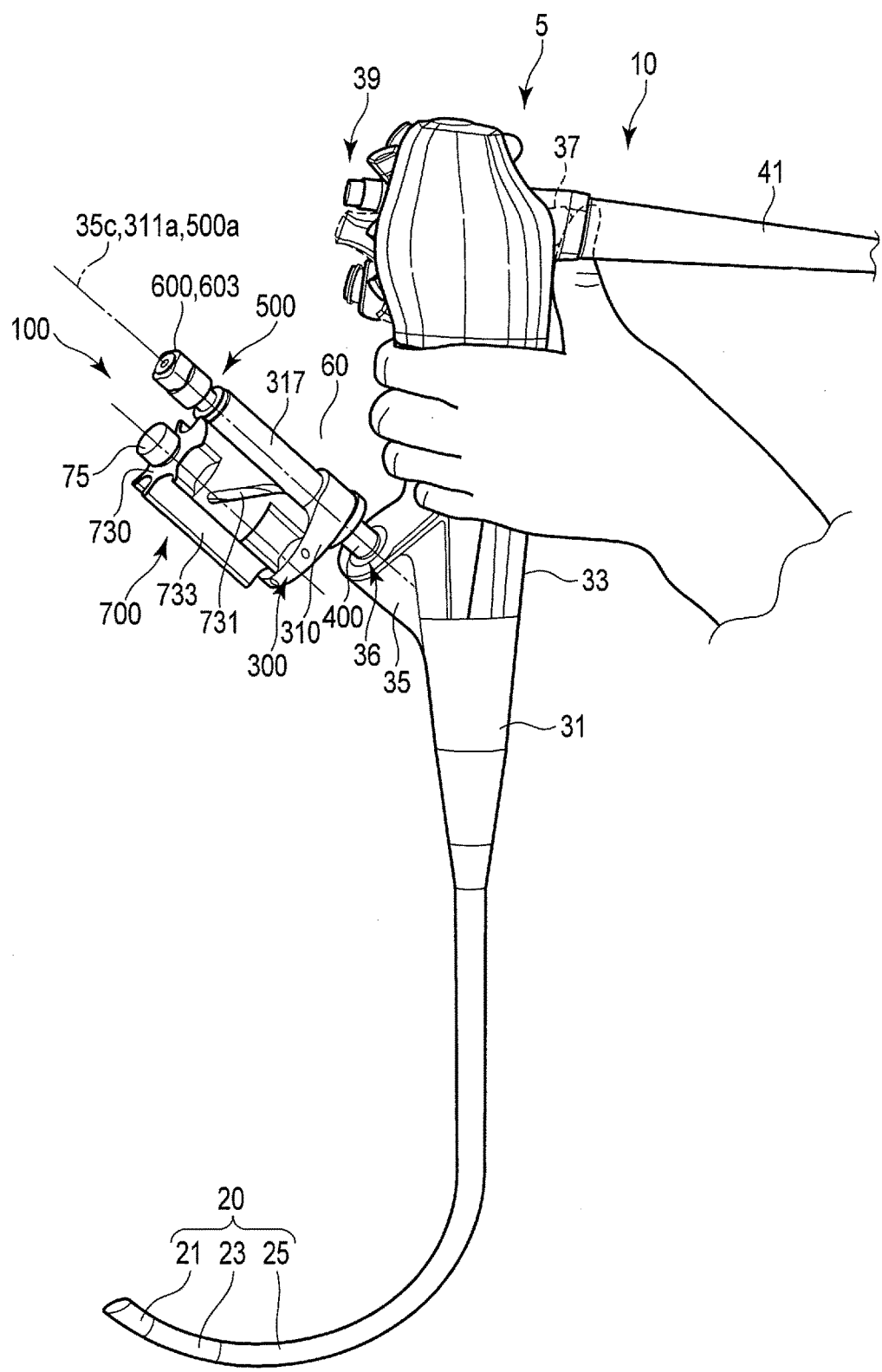
FIG. 5B is a schematic diagram in which the rotary portion is provided outside the clearance, and the prevention of grasping by the advance and retreat assist tool is eliminated, in the endoscope to which the advance and retreat assist tool is attached.

The body portion 410 is not attached to the treatment instrument insertion cap 36 by being fitted into the proximal end portion of the treatment instrument insertion cap 36 in the central axial direction of the treatment instrument insertion cap 36. As shown in FIG. 2C, the cutout portion 413 functions as a head, and the body portion 410 is pressed into the proximal end portion of the treatment instrument insertion cap 36 from the cutout portion 413 in the diametrical direction of the body portion 410. That is, the body portion 410 is pressed into the proximal end portion of the treatment instrument insertion cap 36 from the side surface of the treatment instrument insertion portion 35 via the cutout portion 413 in the diametrical direction of the body portion 410, and is thereby fitted into the proximal end portion of the treatment instrument insertion cap 36, and attached to the proximal end portion of the treatment instrument insertion cap 36. In other words, the proximal end portion of the treatment instrument insertion cap 36 is fitted into the body portion 410 in the diametrical direction of the body portion 410 via the cutout portion 413. Thus, the body portion 410 is attached to the proximal end portion of the treatment instrument insertion cap 36, and the proximal end portion of the treatment instrument insertion cap 36 is provided inside the body portion 410. In this instance, as shown in FIG. 4A and FIG. 4B, the distal end portion of the body portion 410 formed as the inner flange is caught on the edge portion 36c of the treatment instrument insertion cap 36 formed as the outer flange. In this state, as shown in FIG. 5A, FIG. 5B, and FIG. 5C, the body portion 410 is rotatable relative to the treatment instrument insertion cap 36 around the central axis 35c of the treatment instrument insertion hole portion 35a.

When the body portion 410 is detached from the treatment instrument insertion cap 36, the body portion 410 is pulled relative to the proximal end portion of the treatment instrument insertion cap 36 in the diametrical direction of the body portion 410 via the cutout portion 413 and then detached from the proximal end portion of the treatment instrument insertion cap 36, in reverse order from the above.

[Support Portion 430]

As shown in FIG. 2C, FIG. 4A, and FIG. 4B, in the support portion 430 which supports the base member 310 of the base unit 300, the support portion 430 is attached to the body portion 410 so that the first central axis 311a of the first hole portion 311 is provided coaxially with the central axis 35c of the treatment instrument insertion hole portion 35a and so that the first hole portion 311 faces the treatment instrument insertion hole portion 35a.

As shown in FIG. 2C, FIG. 4A, and FIG. 4B, the support portion 430 has a distal end portion which is screwed into the body portion 410, and a proximal end portion which is screwed into the second hole portion 315 and thereby supports the base member 310. The proximal end portion is screwed into the second hole portion 315 so that the support portion 430 communicates with the first hole portion 311.

As shown in FIG. 2C, FIG. 4A, and FIG. 4B, the support portion 430 has a watertight member 433 which is provided inside the proximal end portion of the support portion 430 and which keeps the base member 310 and the support portion 430 watertight. The watertight member 433 has, for example, a ring-shaped packing.

As shown in FIG. 2C, the watertight member 433 has a protrusion portion 433a provided in the outer circumferential surface of the watertight member 433. The protrusion portion 433a slides on a slide groove portion 435 formed in the proximal end portion of the support portion 430 when the watertight member 433 is inserted into and removed from the proximal end portion of the support portion 430. The protrusion portion 433a is grasped when the watertight member 433 is inserted into and removed from the proximal end portion of the support portion 430, and is provided to position the watertight member 433 in the circumferential direction of the support portion 430.

[Attachment of Support Portion 430 to Base Member 310]

As shown in FIG. 2C, FIG. 4A, and FIG. 4B, the base member 310 further has a base thread groove portion 315a formed in the inner circumferential surface of the second hole portion 315.

As shown in FIG. 2C, FIG. 4A, and FIG. 4B, the support portion 430 further has a proximal support thread groove portion 437 which is formed in the outer circumferential surface of the support portion 430 and which meshes with the base thread groove portion 315a. The proximal support thread groove portion 437 is provided at the proximal end portion of the support portion 430.

The support portion 430 is screwed into the second hole portion 315 in the central axis direction of the attachment portion 400 as shown in FIG. 2C, FIG. 4A, and FIG. 4B so that the base thread groove portion 315a and the proximal support thread groove portion 437 mesh with each other, and the support portion 430 is thereby attached to the base member 310. Thus, the base member 310 and the support portion 430 are fastened to each other. At the same time, the support portion 430 communicates with the first hole portion 311.

[Base Unit 300 Rotates Around Central Axis 35c of Treatment Instrument Insertion Hole Portion 35a]

As described above, the base member 310 is attached to the support portion 430, the support portion 430 is attached to the body portion 410, and the body portion 410 is attached to the treatment instrument insertion cap 36.

In this state, as shown in FIG. 1C, the central axis direction of the treatment instrument insertion portion 35 is slanted relative to the direction of the central axis 33a of the grasping portion 33.

As shown in FIG. 1C, an angle formed between the direction of the central axis 35c of the treatment instrument insertion hole portion 35a (the direction of the first central axis 311a of the first hole portion 311) and the direction of the central axis 33a of the grasping portion 33 is an angle θ1. The angle θ1 is invariable even if the advance and retreat assist tool 100 including the attachment portion 400 rotates around the central axis of the treatment instrument insertion cap 36.

As shown in FIG. 1C, FIG. 5A, FIG. 5B, and FIG. 5C, when the advance and retreat assist tool 100 is attached, a clearance 60 is formed between the outer cylindrical portion 317 including the first tubular member 500 and the grasping portion 33.

As shown in FIG. 1C, FIG. 5A, FIG. 5B, and FIG. 5C, the first central axis 311a, the second central axis 500a, and the central axis 35c of the treatment instrument insertion hole portion 35a function as the rotation central axis of the base member 310 when the base member 310 rotates around the central axis 35c of the treatment instrument insertion hole portion 35a. When the base member 310 rotates around the central axis 35c of the treatment instrument insertion hole portion 35a, the rotary portion 700 including the third central axis 700a rotates around the rotation central axis to be provided inside the clearance 60 closer to the grasping portion 33 or to be provided outside the clearance 60 away from the grasping portion 33.

As shown in FIG. 1C, FIG. 5A, FIG. 5B, and FIG. 5C, the state in which the rotary portion 700 is provided inside the clearance 60 is an inside state, and the state in which the rotary portion 700 is provided outside the clearance 60 is an outside state.

As shown in FIG. 1A, FIG. 1B, FIG. 1C, FIG. 5A, and FIG. 5C, the rotary portion 700 is close to the grasping portion 33 and adjacent to the grasping portion 33 in the inside state. The inside state shows a state in which the rotary portion 700 is operated to advance and retreat the treatment instrument 51 and in which the endoscope 10 can be grasped and the treatment instrument 51 can be advanced and retreated with one hand at the same time.

As shown in FIG. 1C, FIG. 5B, and FIG. 5C, the rotary portion 700 is located away from the grasping portion 33 in the outside state. The outside state is created when the treatment instrument 51 does not need to be advanced and retreated and when the rotary portion 700 is not operated, and shows a state in which the prevention of grasping by the advance and retreat assist tool 100 is eliminated.

As shown in FIG. 1A, FIG. 1B, FIG. 1C, FIG. 5A, FIG. 5B, and FIG. 5C, the attachment portion 400 attached to the treatment instrument insertion cap 36 rotates around the central axis 35c of the treatment instrument insertion hole portion 35a so that the rotary portion 700 is provided inside the clearance 60 when the rotary portion 700 is operated and so that the rotary portion 700 is provided outside the clearance 60 when the rotary portion 700 is not operated. Thus, the base member 310 and the rotary portion 700 attached to the attachment portion 400 also rotate.

[First Tubular Member 500]

As shown in FIG. 4A and FIG. 4B, the first tubular member 500 has the second central axis 500a. The first tubular member 500 is provided so that the second central axis 500a is provided along the direction of the first central axis 311a and so that the second central axis 500a is provided coaxially with the first central axis 311a. The first tubular member 500 is formed as a cylindrical member into which the treatment instrument 51 is inserted. The treatment instrument 51 is inserted into the first tubular member 500 from a proximal end portion 500c of the first tubular member 500, and is projected from a distal end portion 500b of the first tubular member 500. The first tubular member 500 is inserted into the outer cylindrical portion 317, and slides on the outer cylindrical portion 317. The shaking of the first tubular member 500 is prevented by the outer cylindrical portion 317.

As shown in FIG. 4A, the treatment instrument 51 is directly inserted into the first hole portion 311 when the first tubular member 500 advances. As shown in FIG. 4B, the treatment instrument 51 is inserted into the first hole portion 311 via the second hole portion 313 when the first tubular member 500 retreats. That is, the first tubular member 500 functions as a guide member which guides the treatment instrument 51 to the first hole portion 311.

As shown in FIG. 4A and FIG. 4B, the first tubular member 500 has the above-mentioned second central axis 500a, and the distal end portion 500b which slides on the outer cylindrical portion 317 when the first tubular member 500 advances and retreats. The first tubular member 500 also has the proximal end portion 500c to which a proximal end portion 51b of the treatment instrument 51 is fixed by the fixing portion 600. The first tubular member 500 further has an opening portion 500d which is provided in the circumferential surface of the first tubular member 500 and with which a later-described protrusion portion 801 is engaged.

As shown in FIG. 4A, the distal end portion 500b slides on the outer cylindrical portion 317 toward the distal end portion of the outer cylindrical portion 317 along the direction of the first central axis 311a (the second central axis 500a) so that the first tubular member 500 is in communication with the first hole portion 311 when the first tubular member 500 advances. As shown in FIG. 4B, the distal end portion 500b slides on the outer cylindrical portion 317 toward the proximal end portion of the outer cylindrical portion 317 along the direction of the first central axis 311a (the second central axis 500a) so that the first tubular member 500 faces the first hole portion 311 when the first tubular member 500 retreats. The first tubular member 500 is longer than the outer cylindrical portion 317. Thus, the proximal end portion 500c is always removed from the outer cylindrical portion 317, is exposed and projected outward from the outer cylindrical portion 317, along the direction of the first central axis 311a (the second central axis 500a).

As shown in FIG. 4A, the opening portion 500d is provided at the distal end portion 500b. The opening portion 500d is always exposed from the first hole portion 311. The opening portion 500d is, for example, circular. The opening portion 500d is a through-hole portion which passes through the first tubular member 500 in the thickness direction of the first tubular member 500. One opening portion 500d is provided.

[Fixing Portion 600]

As shown in FIG. 3A, FIG. 3B, FIG. 4A, and FIG. 4B, the fixing portion 600 is provided at the proximal end portion 500c of the first tubular member 500. The fixing portion 600 fixes the proximal end portion 51b of the treatment instrument 51 to the proximal end portion 500c of the first tubular member 500. The fixing portion 600 has a fixing member 605 which is provided at the proximal end portion 500c and through which the treatment instrument 51 is inserted, and a fastening portion 603 through which the treatment instrument 51 is inserted and which functions as a cap to cover the proximal end portion 500c including the fixing member 605 and which fastens the fixing member 605.

The fastening portion 603 rotates around the axis of the fastening portion 603 and thereby compresses the fixing member 605. The fixing member 605 comes into close contact with the proximal end portion 51b of the treatment instrument 51 by compression. As a result, the treatment instrument 51 becomes integral with the first tubular member 500 via the fixing portion 600. The fixing member 605 is formed by, for example, elastic rubber.

[Rotary Portion 700]

As shown in FIG. 1A, FIG. 1B, FIG. 1C, FIG. 3A, FIG. 3B, FIG. 4A, and FIG. 4B, the rotary portion 700 has the third central axis 700a, and rotates around the third central axis 700a. The rotary portion 700 is removably provided in the base unit 300 so that the third central axis 700a is provided parallel to the second central axis 500a in the direction that intersects at right angles with the direction of the second central axis 500a and thus the rotary portion 700 is adjacent to the first tubular member 500.

The rotary portion 700 has a rotation shaft member 710 having the third central axis 700a, and the rotation body member 730 which is provided around the rotation shaft member 710 and which rotates around the third central axis 700a with respect to the rotation shaft member 710.

[Rotation Shaft Member 710]

As shown in FIG. 4A and FIG. 4B, the rotation shaft member 710 is removably fixed to the base unit 300 so that the third central axis 700a is provided parallel to the second central axis 500a in the direction that intersects at right angles with the direction of the second central axis 500a and thus the rotation shaft member 710 is adjacent to the first tubular member 500. The rotation shaft member has, for example, a circular cylindrical shape.

The rotation shaft member 710 has a distal end portion formed as a fixed end which is fitted into the depression portion 319 of the base member 310 and fixed to the base member 310 by, for example, a screw portion 213e. The screw portion 213e is inserted through the side surface of the base member 310, and abuts on the circumferential surface of the distal end portion of the rotation shaft member 710. The rotation of the rotation shaft member 710 around the third central axis 700a is prevented by the screw portion 213e. The depression portion 319 and the rotation shaft member 710 are provided apart from the outer cylindrical portion 317 in the direction that intersects at right angles with the direction of the second central axis 500a so that the rotation body member 730 can rotate around the third central axis 700a.

The rotation shaft member 710 has a length such that the proximal end portion of the rotation shaft member 710 projects outside the proximal end portion of the rotation body member 730 along the direction of the third central axis 700a when the rotation shaft member 710 is inserted in the rotation body member 730 and the distal end portion of the rotation shaft member 710 is fitted in the depression portion 319.

The rotary portion 700 further has a coming-off prevention member 750 which is provided at the proximal end portion of the rotation shaft member 710 projecting from the rotation body member 730 and which prevents the rotation body member 730 from coming off the rotation shaft member 710. The coming-off prevention member 750 is, for example, a cap which covers the proximal end portion of the rotation shaft member 710 and which is thicker than the proximal end portion. The coming-off prevention member 750 covers the proximal end portion of the rotation shaft member 710, and abuts on the top surface of the rotation body member 730 and prevents the rotation body member 730 from coming off. The coming-off prevention member 750 is formed by, for example, rubber or a metal.

[Rotation Body Member 730]

Figure 2D:
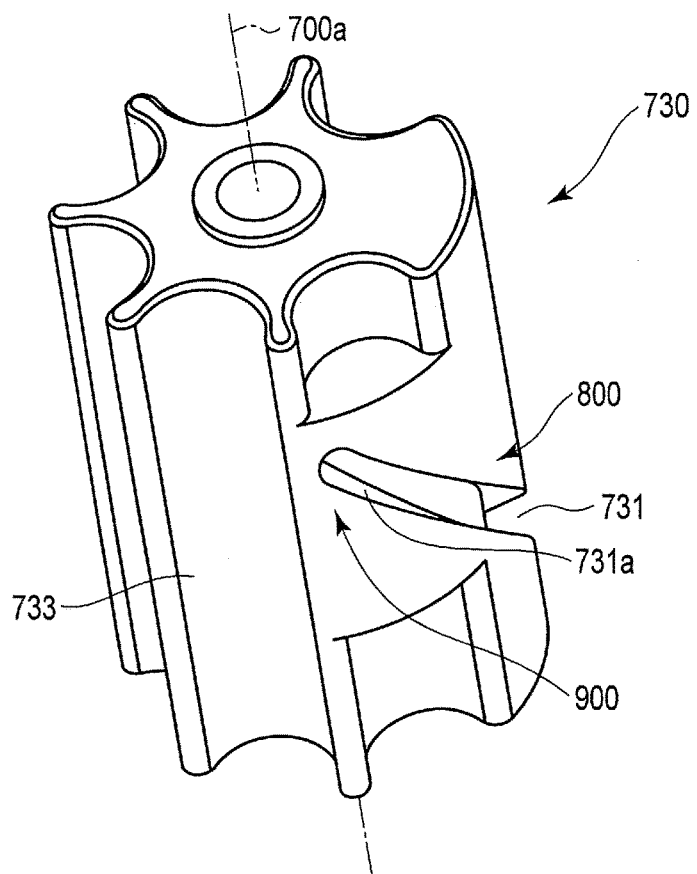
FIG. 2D is a perspective view of a rotation body member.

As shown in FIG. 2D, the rotation body member 730 has a cylindrical shape into which the rotation shaft member 710 is inserted. As shown in FIG. 3A and FIG. 3B, the rotation body member 730 is provided apart from the outer cylindrical portion 317 in the direction that intersects at right angles with the direction of the second central axis 500a. Thus, a clearance portion is formed between the rotation body member 730 and the outer cylindrical portion 317 in the direction that intersects at right angles with the direction of the second central axis 500a. Thus, the rotation body member 730 is rotatable around the third central axis 700a adjacent to the first tubular member 500.

As shown in FIG. 1A, FIG. 1B, FIG. 2D, FIG. 2E, FIG. 3A, and FIG. 3B, the rotation body member 730 has a spiral groove portion 731 which is provided in the outer circumferential surface of the rotation body member 730 to wind around the third central axis 700a and with which the later-described protrusion portion 801 is engaged. Such a rotation body member 730 functions as a cam ring.

As shown in FIG. 1A and FIG. 1B, the rotation body member 730 is provided adjacent to the grasping portion 33 when the advance and retreat assist tool 100 is attached to the endoscope 10. Thus, the rotation body member 730 functions as an operation knob.

As shown in FIG. 1A, FIG. 1B, FIG. 2D, FIG. 2E, FIG. 3A, and FIG. 3B, the rotation body member 730 further has recess portions 733 which are provided in the outer circumferential surface of the rotation body member 730 to avoid the spiral groove portion 731 and on which the fingers of the hand grasping the grasping portion 33 are put. The recess portions 733 are provided along the direction of the third central axis 700a. The recess portions 733 are adjacent to each other in a direction around the third central axis 700a. The inner circumferential surface of the recess portion 733 is, for example, smoothly semicircular. As shown in FIG. 5, the recess portions 733 are formed as grasping surfaces by which the fingers of the left hand can mount the grasping portion 33.

[Configuration of Advance and Retreat Mechanism 800]

The advance and retreat mechanism 800 is provided in the rotary portion 700, the first tubular member 500, and the outer cylindrical portion 317, converts the rotation force of the rotary portion 700 to an advance and retreat force of the first tubular member 500, and transmits the advance and retreat force to the first tubular member 500 and thereby advances and retreats the first tubular member 500 along the direction of the second central axis 500a when the rotary portion 700 rotates.

As shown in FIG. 2A, FIG. 2B, FIG. 3A, FIG. 3B, FIG. 4A, and FIG. 4B, the advance and retreat mechanism 800 has the protrusion portion 801, the spiral groove portion 731, and a rotation prevention member 805.

[Protrusion Portion 801]

As shown in FIG. 2B, FIG. 3A, FIG. 3B, FIG. 4A, and FIG. 4B, in the second central axis 500a and the third central axis 700a that are provided parallel to each other, the protrusion portion 801 is provided straight along the diametrical direction of the first tubular member 500 so that the protrusion portion 801 is provided between the second central axis 500a and the third central axis 700a along the diametrical direction of the first tubular member 500. Thus, the protrusion portion 801 intervenes between the first tubular member 500 (the outer cylindrical portion 317) and the rotary portion 700.

One end portion of the protrusion portion 801 is engaged with the opening portion 500d through the long opening portion 317a, so that the protrusion portion 801 is engaged with part of the circumferential surface of the first tubular member 500. The other end portion face of the protrusion portion 801 is engaged with the spiral groove portion 731 through the long opening portion 317a. The protrusion portion 801 has a diameter such that the protrusion portion 801 abuts on the opening portion 500d, the edge portion of the long opening portion 317a, and the edge of the spiral groove portion 731.

[Spiral Groove Portion 731]

As shown in FIG. 3A and FIG. 3B, the spiral groove portion 731 is provided in the outer circumferential surface of the rotation body member 730 which is provided in the rotary portion 700 to wound around the third central axis 700a, and is engaged with the protrusion portion 801, as described above.

The spiral groove portion 731 is not provided over the whole circumference of the rotation body member 730, but is provided in the shape of a quarter to half arc. A proximal end portion 731a of the spiral groove portion 731 is provided lower than the proximal end portion of the rotation body member 730, and a distal end portion 731b of the spiral groove portion 731 is provided at the distal end portion of the rotation body member 730. The spiral groove portion 731 does not pass through the rotation body member 730 in the direction of the third central axis 700a. The spiral groove portion 731 does not pass through the rotation body member 730 in the thickness direction of the rotation body member 730.

The length of the spiral groove portion 731 or the length from the proximal end portion 731a of the spiral groove portion 731 to the distal end portion 317c of the long opening portion 317a corresponds to the movement amount of the protrusion portion 801, corresponds to the movement amount of the first tubular member 500, and corresponds to the advance and retreat amount of the treatment instrument 51. These are substantially equal in size to one another. The maximum value of the length corresponds to the maximum value of the movement amount and the maximum value of the advance and retreat amount. Each of these maximum values corresponds to the size of the part to be treated with the treatment instrument 51, and has a desired value. The maximum value is, for example, 30 mm.

[Rotation Prevention Member 805]

The rotation prevention member 805 is provided in the base member 310 of the base unit 300, and prevents the rotation of the first tubular member 500 around the second central axis 500a.

As shown in FIG. 2B, as described above, the rotation prevention member 805 has the outer cylindrical portion 317 which is provided in the base member 310 of the base unit 300 and into which first tubular member 500 is inserted, and the long opening portion 317a which is provided in the outer cylindrical portion 317 along the direction of the second central axis 500a, which the protrusion portion 801 passes through in the diametrical direction of the first tubular member 500 to engage with the spiral groove portion 731 and which the protrusion portion 801 slides along the direction of the central axis 500a.

[Operation of Advance and Retreat Mechanism 800]

As shown in FIG. 1A, FIG. 1B, FIG. 3A, FIG. 3B, FIG. 4A, and FIG. 4B, if the rotation body member 730 of the rotary portion 700 rotates around the third central axis 700a, the spiral groove portion 731 provided in the rotation body member 730 also rotates simultaneously.

As shown in FIG. 3A and FIG. 3B, the protrusion portion 801 is in abutment with the edge portion of the spiral groove portion 731. Thus, in response to the rotation of the spiral groove portion 731, the protrusion portion 801 is pressed to rotate by the spiral groove portion 731. As shown in FIG. 2B, the protrusion portion 801 is inserted through the long opening portion 317a of the rotation prevention member 805, and is also in abutment with the edge portion of the long opening portion 317a. Thus, the protrusion portion 801 is pressed to rotate by the spiral groove portion 731, so that the protrusion portion 801 moves in the long opening portion 317a along the direction of the second central axis 500a.

Thus, the spiral groove portion 731 rotates in response to the rotation of the rotation body member 730 of the rotary portion 700. As a result of the rotation of the spiral groove portion 731, the protrusion portion 801 moves in the long opening portion 317a along the direction of the second central axis 500a by the spiral groove portion 731.

As shown in FIG. 2B, the protrusion portion 801 abuts on the edge portion of the long opening portion 317a, so that the first tubular member 500 with which the protrusion portion 801 is engaged is prevented from rotating around the second central axis 500a.

As shown in FIG. 3A, FIG. 3B, FIG. 4A, and FIG. 4B, the spiral groove portion 731 rotates, and the protrusion portion 801 moves in the long opening portion 317a along the direction of the second central axis 500a, so that the first tubular member 500 advances and retreats along the direction of the second central axis 500a while the rotation of the first tubular member 500 around the second central axis 500a is prevented. As a result, the treatment instrument 51 fixed to the first tubular member 500 advances and retreats.

That is, the spiral groove portion 731 rotates, and the spiral groove portion 731 thereby advances and retreats the first tubular member 500 along the direction of the second central axis 500a via the protrusion portion 801 in the first tubular member 500 which is prevented from rotating around the second central axis 500a by the outer cylindrical portion 317 of the rotation prevention member 805 and the long opening portion 317a.

As shown in FIG. 4A and FIG. 4B, the rotation shaft member 710 is fixed to the base member 310 by, for example, a screw portion 213e. Therefore, the rotation shaft member 710 remains fixed without being affected by the rotation of the rotation body member 730.

As shown in FIG. 2B, the protrusion portion 801 only moves in the long opening portion 317a along the direction of the second central axis 500a. Therefore, the first tubular member 500 only advances and retreats along the direction of the second central axis 500a, and the rotation of the first tubular member 500 around the second central axis 500a is prevented. Similarly, the treatment instrument 51 only advances and retreats, and the rotation of the treatment instrument 51 around the second central axis 500a is prevented.

Thus, the advance and retreat mechanism 800 advances and retreats the treatment instrument 51 while the treatment instrument 51 is prevented from rotating around the second central axis 500a in response to the rotation of the rotary portion 700 around the third central axis 700a when the rotary portion 700 rotates around the third central axis 700a.

[Regulating Mechanism 900]

The regulating mechanism 900 regulates the advance and retreat of the first tubular member 500 when the first tubular member 500 advances and retreats along the direction of the second central axis 500a so that the distal end portion 500b of the first tubular member 500 moves along the direction of the second central axis 500a between a part where the first hole portion 311 provided on the distal end portion side of the outer cylindrical portion 317 is in communication with the first tubular member 500 and a position on the side where the first tubular member 500 provided on the proximal end portion side of the outer cylindrical portion 317 comes off the outer cylindrical portion 317.

As shown in FIG. 2B and FIG. 2D, the regulating mechanism 900 is formed by the protrusion portion 801, the edge portion of the proximal end portion 731a of the spiral groove portion 731, and the edge portion of the distal end portion 317c of the long opening portion 317a.

[Lock Mechanism 950]

The advance and retreat assist tool 100 further has a lock mechanism 950 which is provided in the rotary portion 700 and which locks an inadvertent rotation of the rotation body member 730.

Figure 2E:
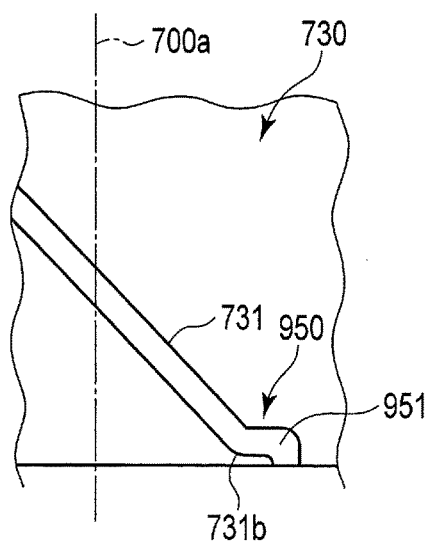
FIG. 2E is a diagram showing a distal end portion of a spiral groove portion and an outside communication groove portion at a distal end portion of the rotation body member.

As shown in FIG. 2E, the lock mechanism 950 has an outside communication groove portion 951 which is provided in the outer circumferential surface of the distal end portion of the rotation body member 730 to be in communication with the distal end portion 731b of the spiral groove portion 731 and which is provided along the direction around the third central axis 700a. Part of the outside communication groove portion 951 is in communication with the outside in the direction of the third central axis 700a so that the protrusion portion 801 is inserted and removed from the outside. The outside communication groove portion 951 is also provided so that the protrusion portion 801 is engaged with the spiral groove portion 731.

The first tubular member 500 with which the protrusion portion 801 is engaged is inserted into the outer cylindrical portion 317 so that the protrusion portion 801 slides in the long opening portion 317a. In this state, the rotation body member 730 is put into the rotation shaft member 710 so that the protrusion portion 801 is inserted into the outside communication groove portion 951. When the protrusion portion 801 is engaged with the outside communication groove portion 951, the lock mechanism 950 locks the rotation of the rotation body member 730.

When the rotation body member 730 then rotates around the third central axis 700a, the protrusion portion 801 moves to the distal end portion 731b of the spiral groove portion 731 from the outside communication groove portion 951 and is then engaged with the spiral groove portion 731.

[Functions]

[Attachment of Advance and Retreat Assist Tool 100 to Endoscope 10]

As shown in FIG. 1A, FIG. 1B, FIG. 4A, and FIG. 4B, the fixing unit 400 fixes the base unit 300 to the endoscope 10 so that the first hole portion 311 faces the treatment instrument insertion hole portion 35a.

At the same time, as has been described in [Attachment of Body Portion 410 to Treatment Instrument Insertion Cap 36], the body portion 410 is pressed into the proximal end portion of the treatment instrument insertion cap 36 from the side surface of the treatment instrument insertion portion 35 via the cutout portion 413 in the diametrical direction of the body portion 410 as shown in FIG. 2C, FIG. 4A, and FIG. 4B, and is thereby attached to the proximal end portion of the treatment instrument insertion cap 36.

As has been described in [Attachment of Support Portion 430 to Base Member 310], the support portion 430 is then screwed into the second hole portion 315 in the central axis direction of the attachment portion 400 as shown in FIG. 2C, FIG. 4A, and FIG. 4B so that the base thread groove portion 315a and the proximal support thread groove portion 437 mesh with each other, and the support portion 430 is thereby attached to the base member 310. Thus, the base member 310 and the support portion 430 are fastened to each other.

As has been described in [Attachment of Body Portion 410 and Support Portion 430], the support portion 430 is then screwed into the body thread groove portion 411 in the central axis direction of the attachment portion 400 as shown in FIG. 2C, FIG. 4A, and FIG. 4B so that the body thread groove portion 411 and the distal support thread groove portion 431 mesh with each other, and the support portion 430 is thereby attached to the body portion 410. Thus, the body portion 410 and the support portion 430 are fastened to each other.

In the attachment described above, the order of attachment is not specifically limited. Consequently, the advance and retreat assist tool 100 is attached to the treatment instrument insertion cap 36.

As shown in FIG. 1A, FIG. 1B, FIG. 1C, FIG. 5A, and FIG. 5C, the body portion 410 rotates around the central axis 35c of the treatment instrument insertion hole portion 35a after the body portion 410 and the support portion 430 have been temporarily unfastened from each other so that, for example, the rotary portion 700 including the third central axis 700a is provided inside the clearance 60. The body portion 410 and the support portion 430 are then fastened to each other again. The rotary portion 700 is then provided inside the clearance 60, and adjoins the grasping portion 33.

As shown in FIG. 5C, for example, the whole rotary portion 700 is provided inside the clearance 60, so that, for example, the rotary portion 700 is operated by the little finger or third finger of the left hand of the surgeon grasping the grasping portion 33.

As shown in FIG. 5C, part of the rotary portion 700 is provided inside the clearance 60, so that, for example, the rotary portion 700 is operated by the middle finger of the left hand of the surgeon grasping the grasping portion 33.

Thus, the ratio of the rotary portion 700 to be provided in the clearance 60 changes depending on, for example, the size of the left hand or the lengths of the fingers. That is, the location of the rotary portion 700 is properly adjusted by the surgeon when the rotary portion 700 is operated.

[Provision of Treatment Instrument 51]

After the insertion portion 20 of the endoscope 10 is inserted into the body cavity, the treatment instrument 51 is inserted from the fixing portion 600, and inserted through the first tubular member 500, as shown in FIG. 1A and FIG. 1B. The treatment instrument 51 is further inserted into the endoscope 10 from the treatment instrument insertion portion 35. As shown in FIG. 1A and FIG. 1B, the distal end portion 51a of the treatment instrument 51 then projects from the distal opening portion 35b. The length of the projecting distal end portion 51a of the treatment instrument 51 is a desired length.

The fastening portion 603 rotates around the axis of the fastening portion 603 and thereby fastens the cylindrical portion 601, and compresses the fixing member 605 by fastening. The fixing member 605 comes into close contact with the proximal end portion 51b of the treatment instrument 51 by compression. As a result, the treatment instrument 51 is fixed to the advance and retreat assist tool 100 via the fixing portion 600 and the first tubular member 500.

[Grasping of Endoscope 10 and Treatment Instrument 51]

As shown in FIG. 5A, the grasping portion 33 is grasped by the left hand of the surgeon, the rotary portion 700 adjacent to the grasping portion 33 is operated by, for example, the little finger or third finger of the left hand, and the bending operation portion is operated by the thumb of the left hand. In this instance, the rotary portion 700 is provided inside the clearance 60, so that the rotary portion 700 is provided adjacent to the grasping portion 33. The endoscope 10 is grasped and the treatment instrument 51 is advanced and retreated with one hand at the same time.

[Advance Operation of Treatment Instrument 51]

When the rotary portion 700 is operated by, for example, the little finger or third finger of the left hand, the rotary portion 700 rotates in one direction around the third central axis 700a. At the same time, the spiral groove portion 731 also rotates in the same manner as the rotary portion 700.

As shown in FIG. 3A and FIG. 4A, as a result of the rotation of the spiral groove portion 731, the protrusion portion 801 moves toward the distal end portion 317c of the long opening portion 317a in the long opening portion 317a along the direction of the second central axis 500a by the spiral groove portion 731.

In this instance, as shown in FIG. 2B, the protrusion portion 801 abuts on the edge portion of the long opening portion 317a, so that the first tubular member 500 with which the protrusion portion 801 is engaged is prevented from rotating around the second central axis 500a.

The spiral groove portion 731 then rotates, and the protrusion portion 801 moves toward the distal end portion 317c in the long opening portion 317a along the direction of the second central axis 500a, so that the first tubular member 500 advances along the direction of the second central axis 500a while the rotation of the first tubular member 500 around the second central axis 500a is prevented. As a result, the treatment instrument 51 fixed to the first tubular member 500 advances.

Since the outer cylindrical portion 317 integrated with the base member 310 is fixed, the long opening portion 317a is fixed, so that the long opening portion 317a is prevented from rotating in the same manner as the spiral groove portion 731. Therefore, the protrusion portion 801 only moves in the long opening portion 317a along the direction of the second central axis 500a. Therefore, the first tubular member 500 only advances along the direction of the second central axis 500a, and the rotation of the first tubular member 500 around the second central axis 500a is prevented. Similarly, the treatment instrument 51 only advances, and the rotation of the treatment instrument 51 around the second central axis 500a is prevented.

The protrusion portion 801 abuts on the distal end portion 317c of the long opening portion 317a included in the regulating mechanism 900 or the edge portion of the distal end portion 731b of the spiral groove portion 731, so that the advance of the first tubular member 500 is stopped, and the advance of the treatment instrument 51 is stopped.

[Retreat Operation of Treatment Instrument 51]

When the rotary portion 700 is operated by, for example, the little finger or third finger of the left hand, the rotary portion 700 rotates in the other direction around the third central axis 700a. At the same time, the spiral groove portion 731 also rotates in the same manner as the rotary portion 700.

As shown in FIG. 3B and FIG. 4B, as a result of the rotation of the spiral groove portion 731, the protrusion portion 801 moves toward the distal end portion 317c of the long opening portion 317a in the long opening portion 317a along the direction of the second central axis 500a by the spiral groove portion 731.

In this instance, the protrusion portion 801 abuts on the edge portion of the long opening portion 317a, so that the first tubular member 500 with which the protrusion portion 801 is engaged is prevented from rotating around the second central axis 500a.

The spiral groove portion 731 then rotates, and the protrusion portion 801 moves toward the proximal end portion 317b in the long opening portion 317a along the direction of the second central axis 500a, so that the first tubular member 500 retreats along the direction of the second central axis 500a while the rotation of the first tubular member 500 around the second central axis 500a is prevented. As a result, the treatment instrument 51 fixed to the first tubular member 500 retreats.

Since the outer cylindrical portion 317 integrated with the base member 310 is fixed, the long opening portion 317a is fixed, so that the long opening portion 317a is prevented from rotating in the same manner as the spiral groove portion 731. Therefore, the protrusion portion 801 only moves in the long opening portion 317a along the direction of the second central axis 500a. Therefore, the first tubular member 500 only retreats along the direction of the second central axis 500a, and the rotation of the first tubular member 500 around the second central axis 500a is prevented. Similarly, the treatment instrument 51 only retreats, and the rotation of the treatment instrument 51 around the second central axis 500a is prevented.

The protrusion portion 801 abuts on the edge portion of the proximal end portion 731a of the spiral groove portion 731 included in the regulating mechanism 900, so that the retreat of the first tubular member 500 is stopped, and the retreat of the treatment instrument 51 is stopped. This also prevents the first tubular member 500 from coming off the outer cylindrical portion 317.

[When Advance and Retreat Operations of Treatment Instrument 51 are not Needed]

As shown in FIG. 1C, FIG. 5B, and FIG. 5C, the attachment portion 400 attached to the treatment instrument insertion cap 36 rotates around the central axis 35c of the treatment instrument insertion hole portion 35a so that the rotary portion 700 is provided outside the clearance 60. As a result, the advance and retreat assist tool 100 including the attachment portion 400 also rotates. As shown in FIG. 1C, FIG. 5B, and FIG. 5C, the rotary portion 700 is provided outside the clearance 60, so that the rotary portion 700 separates from the grasping portion 33. Thus, the interruption of the grasping by the advance and retreat assist tool 100 is eliminated.

The attachment portion 400 rotates as described above after the treatment instrument 51 is removed from the endoscope 10.

The attachment portion 400 also rotates as described above after the body portion 410 and the support portion 430 have been temporarily unfastened from each other. The body portion 410 and the support portion 430 will then be fastened to each other again.

When the attachment portion 400 rotates, rotational resistance applied to the inner circumferential surface of the distal end portion of the body portion 410 by the edge portion of the treatment instrument insertion cap 36 is reduced by the cutout portion 413.

[Lock Operation]

When the protrusion portion 801 is engaged with the outside communication groove portion 951, the lock mechanism 950 locks the rotation of the rotation body member 730. The lock operation is performed to prevent unnecessary rotation of the rotary portion 700, for example, when the advance and retreat operations of the treatment instrument 51 are not needed. The lock operation is also performed to fix the treatment instrument 51 when the treatment instrument 51 has advanced to the maximum.

[Disassembly of Advance and Retreat Assist Tool 100]

One example of the disassembly of the advance and retreat assist tool 100 is shown below.

The rotation body member 730 rotates, the protrusion portion 801 moves to the outside communication groove portion 951, and the coming-off prevention member 750 is detached. The rotation body member 730 is removed from the rotation shaft member 710 so that the protrusion portion 801 is taken off the outside communication groove portion 951. The screw portion 213e is taken out, and the rotation shaft member 710 is detached from the base member 310.

While the treatment instrument 51 is detached, the first tubular member 500 including the protrusion portion 801 is removed from the outer cylindrical portion 317.

As described above, the attachment portion 400 is detached from the treatment instrument insertion cap 36, and the base member 310 is detached from the attachment portion 400.

The advance and retreat assist tool 100 is disassembled as above.

[Advantageous Effects]

Thus, according to the present embodiment, the attachment portion 400 attaches the base unit 300 to the treatment instrument insertion portion 35 so that the base unit 300 is rotatable around the central axis 35c of the treatment instrument insertion hole portion 35a. According to the present embodiment, the rotary portion 700 is removably provided in the base unit 300 to adjacent to the first tubular member 500.

Thus, according to the present embodiment, as shown in FIG. 1A, FIG. 1B, FIG. 1C, FIG. 5A, FIG. 5B, and FIG. 5C, the rotary portion 700 is provided inside or outside the clearance 60 around the rotation central axis of the base member 310.

The rotary portion 700 is provided inside the clearance 60, so that as shown in FIG. 1A, FIG. 1B, FIG. 1C, FIG. 5A, and FIG. 5C, according to the present embodiment, the fingers of the hand grasping the grasping portion 33 surely reach the rotary portion 700 without fail, the surgeon is not burdened, handling is easier, and the endoscope 10 can be grasped and the treatment instrument 51 can be advanced and retreated with one hand at the same time. Moreover, according to the present embodiment, it is possible to prevent the whole endoscope 10 from increasing in size without causing problems to the smooth one-handed advance and retreat operations.

As shown in FIG. 5B and FIG. 5C, the rotary portion 700 is provided outside the clearance 60. Thus, according to the present embodiment, as shown in FIG. 5B and FIG. 5C, when the treatment instrument 51 is not advanced and retreated, the interruption of the grasping by the advance and retreat assist tool 100 is eliminated.

Thus, according to the present embodiment, operability of the advance and retreat assist tool 100 improves.

According to the present embodiment, the rotary portion 700 is attachable to and detachable from base member 310, the base unit 300 is attachable to and detachable from the treatment instrument insertion cap 36 by the attachment portion 400, and the first tubular member 500 is removable from the outer cylindrical portion 317. Thus, according to the present embodiment, the advance and retreat assist tool 100 can be easily disassembled.

Thus, according to the present embodiment, the structure associated with disassembly for, for example, cleaning can be simpler.

As described above, according to the present embodiment, both the simpler structure and operability can be provided in the advance and retreat assist tool 100. The present embodiment also enables simple one-handed operations and smooth one-handed advance and retreat operations, and enables the advance and retreat assist tool 100 to rotate around the central axis 35*c* of the treatment instrument insertion hole portion 35*a* in accordance with procedures.

According to the present embodiment, as shown in FIG. 1A, FIG. 1B, FIG. 1C, FIG. 5A, and FIG. 5C, the rotary portion 700 is provided inside the clearance 60, so that the rotary portion 700 can be provided adjacent to the grasping portion 33. Thus, the present embodiment ensures that the fingers of one hand grasping the grasping portion 33 can surely reach the rotary portion 700 and that the treatment instrument 51 can be surely advanced and retreated while the grasping portion 33 is grasped. According to the present embodiment, the surgeon can grasp the endoscope 10 and advance and retreat the treatment instrument 51 with one hand. According to the present embodiment, it is possible to prevent the endoscope 10 from increasing in size.

According to the present embodiment, as shown in FIG. 1C, FIG. 5B, and FIG. 5C, the rotary portion 700 is provided outside the clearance 60, so that the interruption of the grasping by the advance and retreat assist tool 100 can be eliminated when the treatment instrument 51 is not advanced and retreated.

According to the present embodiment, the bending operation portion 37 and the switch portion 39 are provided in the grasping portion 33. Thus, according to the present embodiment, the surgeon can operate the bending operation portion 37 and the switch portion 39 while grasping the endoscope 10 and advancing and retreating the treatment instrument 51 with one hand at the same time.

According to the present embodiment, the advance and retreat mechanism 800 converts the rotation force of the rotary portion 700 to the advance and retreat force, and advances and retreats the first tubular member 500 by the advance and retreat force. Thus, according to the present embodiment, it is possible to prevent the size increase of the endoscope 10, ensure that the treatment instrument 51 is finely advanced and retreated by one hand grasping the grasping portion 33, and prevent a burden on the surgeon.

More specifically, according to the present embodiment, in the advance and retreat mechanism 800, the rotation force of the rotary portion 700 is not transmitted directly to the first tubular member 500, but converted to the advance and retreat force by the protrusion portion 801, the spiral groove portion 731, the outer cylindrical portion 317, and the long opening portion 317*a*, and transmitted indirectly to the first tubular member 500. Thus, according to the present embodiment, it is possible to prevent the treatment instrument 51 from rapidly advancing and retreating, and finely advance and retreat the treatment instrument 51.

According to the present embodiment, the treatment instrument 51 can be advanced and retreated without rotating together with the rotary portion 700 by the rotation prevention member 805 of the advance and retreat mechanism 800.

According to the present embodiment, in the regulating mechanism 900, the protrusion portion 801 abuts on the edge portion of the distal end portion 317*c* of the long opening portion 317*a* and the edge of the proximal end portion 731*a* of the spiral groove portion 731, so that the advance and retreat of the first tubular member 500 can be regulated, and the advance and retreat of the treatment instrument 51 can be regulated.

The long opening portion 317*a* may have a length slightly smaller than the length from one edge portion of the spiral groove portion 731 to the other edge portion in the direction of the second central axis 500*a*. In this case, the protrusion portion 801 abuts on the edge portion of the proximal end portion 317*b* of the long opening portion 317*a* and the edge portion of the distal end portion 317*c*, so that the advance and retreat of the first tubular member 500 can be regulated, and the advance and retreat of the treatment instrument 51 can be regulated. The regulating mechanism 900 is then formed by the protrusion portion 801 and the long opening portion 317*a*.

The long opening portion 317*a* may have a length substantially equal to the length from one edge portion of the spiral groove portion 731 to the other edge portion in the direction of the second central axis 500*a*. In this case, one edge portion of the long opening portion 317*a* faces one edge portion of the spiral groove portion 731, and the other edge portion of the long opening portion 317*a* faces the other edge portion of the spiral groove portion 731. In this case, the protrusion portion 801 abuts on the edge portion of the long opening portion 317*a* and the edge portion of the spiral groove portion 731, so that the advance and retreat of the first tubular member 500 can be regulated, and the advance and retreat of the treatment instrument 51 can be regulated. The regulating mechanism 900 is then formed by the protrusion portion 801, the long opening portion 317*a*, and the spiral groove portion 731.

Thus, the regulating mechanism 900 has only to be formed by the protrusion portion 801 and at least one of the spiral groove portion 731 and long opening portion 317*a*.

According to the present embodiment, the proximal end portion 500*c* of the first tubular member 500 is always removed from the outer cylindrical portion 317, exposed from the outer cylindrical portion 317, and projects outside the outer cylindrical portion 317. Thus, according to the present embodiment, the treatment instrument 51 can be easily fixed to the first tubular member 500.

According to the present embodiment, the outer cylindrical portion 317 can prevent the first tubular member 500 from moving in a direction that intersects at right angles with the direction of the second central axis 500*a*. Thus, according to the present embodiment, the first tubular member 500 and the treatment instrument 51 can be advanced and retreated.

According to the present embodiment, it is possible to freely adjust the advance and retreat amount of the treatment instrument 51 by setting the length of the long opening portion 317*a* and the length of the spiral groove portion 731 to desired lengths.

According to the present embodiment, for example, the first tubular member 500 may have an unshown index portion which is provided on the outer circumferential surface of the first tubular member 500 and which indicates the advance and retreat position of the treatment instrument 51. When the first tubular member 500 is exposed from the outer cylindrical portion 317 in accordance with the advance and retreat, the index portion is exposed from the outer cylindrical portion 317. Thus, the surgeon can recognize the advance and retreat position of the treatment instrument 51 by checking the index portion.

According to the present embodiment, the rotation shaft member 710 and the rotation body member 730 are attachable to and detachable from the base unit 300, and can be exchangeable. The rotation shaft member 710 may be integrated with the base member 310.

According to the present embodiment, the recess portions 733 are provided to avoid the spiral groove portion 731. Thus, according to the present embodiment, it is possible to prevent the fingers from being put on the spiral groove portion 731 when the fingers are put on the recess portions 733 for the operation of the rotary portion 700. According to the present embodiment, it is also possible to prevent the rotation force of the rotary portion 700 from not being transmitted to the first tubular member 500 as the advance and retreat force due to the fingers.

According to the present embodiment, the coming-off prevention member 750 can prevent the rotation body member 730 from coming off the rotation shaft member 710.

According to the present embodiment, when the protrusion portion 801 is engaged with the outside communication groove portion 951, the rotation of the rotation body member 730 can be locked. Thus, according to the present embodiment, the treatment instrument 51 can be fixed.

According to the present embodiment, as shown in FIG. 2C, FIG. 4A, and FIG. 4B, the support portion 430 is screwed into the body portion 410 attached to the treatment instrument insertion cap 36. The support portion 430 then presses the edge portion of the treatment instrument insertion hole portion 35a into the body portion 410, and the attachment portion 400 is fixed to the treatment instrument insertion portion 35. As a result, according to the present embodiment, the fixing of the advance and retreat assist tool 100 to the endoscope 10 can be ensured, and the advance and retreat assist tool 100 can be easily separated from the endoscope 10. According to the present embodiment, the attachment portion 400 can be easily disassembled, and more efficiently cleaned.

According to the present embodiment, as shown in FIG. 2C, FIG. 4A, and FIG. 4B, the interference prevention member 450 can prevent the support portion 430 and the treatment instrument insertion cap 36 from damaging each other, and the interference prevention member 450 can also keep the support portion 430 and the treatment instrument insertion cap 36 watertight.

According to the present embodiment, as shown in FIG. 2C, FIG. 4A, and FIG. 4B, the advance and retreat assist tool 100 can be easily attached to the treatment instrument insertion cap 36 owing to the cutout portion 413. According to the present embodiment, the distal end portion of the body portion 410 formed as the inner flange can be caught on the edge portion 36c of the treatment instrument insertion cap 36 formed as the outer flange owing to the cutout portion 413. As a result, according to the present embodiment, the support portion 430 can press the edge portion 36c into the body portion 410, as described above. Thus, according to the present embodiment, it is possible to prevent the body portion 410 from coming off the treatment instrument insertion cap 36. According to the present embodiment, rotational resistance can be reduced by the cutout portion 413 when the body portion 410 rotates.

Various modifications can be made to the configuration described above. Examples of the modifications are described below.

[Modification of Rotation Prevention Member 805]

As shown in FIG. 6A, the rotation prevention member 805 has a noncircular hollow portion 500f of the first tubular member 500, and a non-circular-cylindrical inner cylindrical portion 321 which is erected on the base member 310 to be integrated with the base member 310 and which is fitted into the hollow portion 500f. As shown in FIG. 6A, the hollow portion 500f and the inner cylindrical portion 321 are, for example, D-shaped.

As shown in FIG. 6B, the inner cylindrical portion 321 may have a protrusion portion 321a which is provided on an outer circumferential surface of the inner cylindrical portion 321 and which protrudes sideward from the outer circumferential surface. The protrusion portion 321a is provided straight along the axial direction of the inner cylindrical portion 321. For example, the protrusion portion 321a is continuously provided from a distal end portion of the inner cylindrical portion 321 to a proximal end portion of the inner cylindrical portion 321. In this case, the hollow portion 500f has a groove portion 500g which is provided on an inner circumferential surface of the first tubular member 500, which is depressed from the inner circumferential surface toward an outer circumferential surface of the first tubular member 500, and which the protrusion portion 321a slides on and fits into.

In the case described above, the inner cylindrical portion 321 is inserted into the first tubular member 500. When the inner cylindrical portion 321 is fitted into the hollow portion 500f, the rotation of the first tubular member 500 around the second central axis 500a is prevented.

The inner cylindrical portion 321 is in communication with the first hole portion 311. A central axis of the inner cylindrical portion 321 is provided coaxially with the first central axis 311a of the first hole portion 311. The first tubular member 500 slides on the inner cylindrical portion 321 along the direction of the first central axis 311a to advance and retreat the inner cylindrical portion 321. The inner cylindrical portion 321 is shorter than the first tubular member 500.

The inner cylindrical portion 321 may be independent of the base member 310. In this case, how to attach the inner cylindrical portion 321 to the base member 310 is not particularly limited; for example, the distal end portion of the inner cylindrical portion 321 is removably fitted into the first hole portion 311.

In the present modification, in the first tubular member 500 is prevented from rotating around the second central axis 500a, and the first tubular member 500 including the protrusion portion 801 advances and retreats along the direction of the second central axis 500a in response to the rotation of the spiral groove portion 731.

Thus, in the present modification, when the first tubular member 500 advances and retreats, the rotation of the first tubular member 500 around the second central axis 500a can be prevented. According to the present embodiment, it is not necessary to provide the long opening portion 317a in the first tubular member 500, and the configuration of the first tubular member 500 can be simpler.

Thus, the rotation prevention member 805 has the outer cylindrical portion 317 and the long opening portion 317a as has been described in the first embodiment, or has the hollow portion 500f and the inner cylindrical portion 321 as has been described in the modification.

The contents described above are also applicable to the outer cylindrical portion 317 of the rotation prevention member 805 described in the first embodiment. To sum up, the rotation prevention member 805 is formed by the cylindrical portion 317 into which the first tubular member 500 is inserted and which has an inner shape different from the outer shape of the first tubular member 500, or by the cylindrical portion 321 which is inserted into the first tubular member 500 and which has an outer shape different from the inner shape of the first tubular member 500.

The outer cylindrical portion 317 of the rotation prevention member 805 and the long opening portion 317a described in the first embodiment are applicable to the present modification. To sum up, the rotation prevention member 805 is formed by the cylindrical portion 317 into which the first tubular member 500 is inserted and which has the long opening portion 317a where the protrusion portion 801 provided on the outer circumferential surface of the first tubular member 500 slides, or by the cylindrical portion 321 which is inserted into the first tubular member 500 and which has, on its outer circumferential surface, the protrusion portion 321a where the groove portion 500g provided on the inner circumferential surface of the first tubular member 500 slides.

The inner cylindrical portion 321 holds the first tubular member 500 so that the second central axis 500a is provided coaxially with the first central axis 311a, so that the first tubular member 500 advances and retreats along the direction of the second central axis 500a, so that the movement of the first tubular member 500 in the direction that intersects at right angles with the direction of the second central axis 500a is prevented, and so that the shaking of the first tubular member 500 is prevented. In this case, the inside diameter of the first tubular member 500 is substantially the same as the outside diameter of the inner cylindrical portion 321.

[First Modification of Lock Mechanism 950]

Figure 7A:
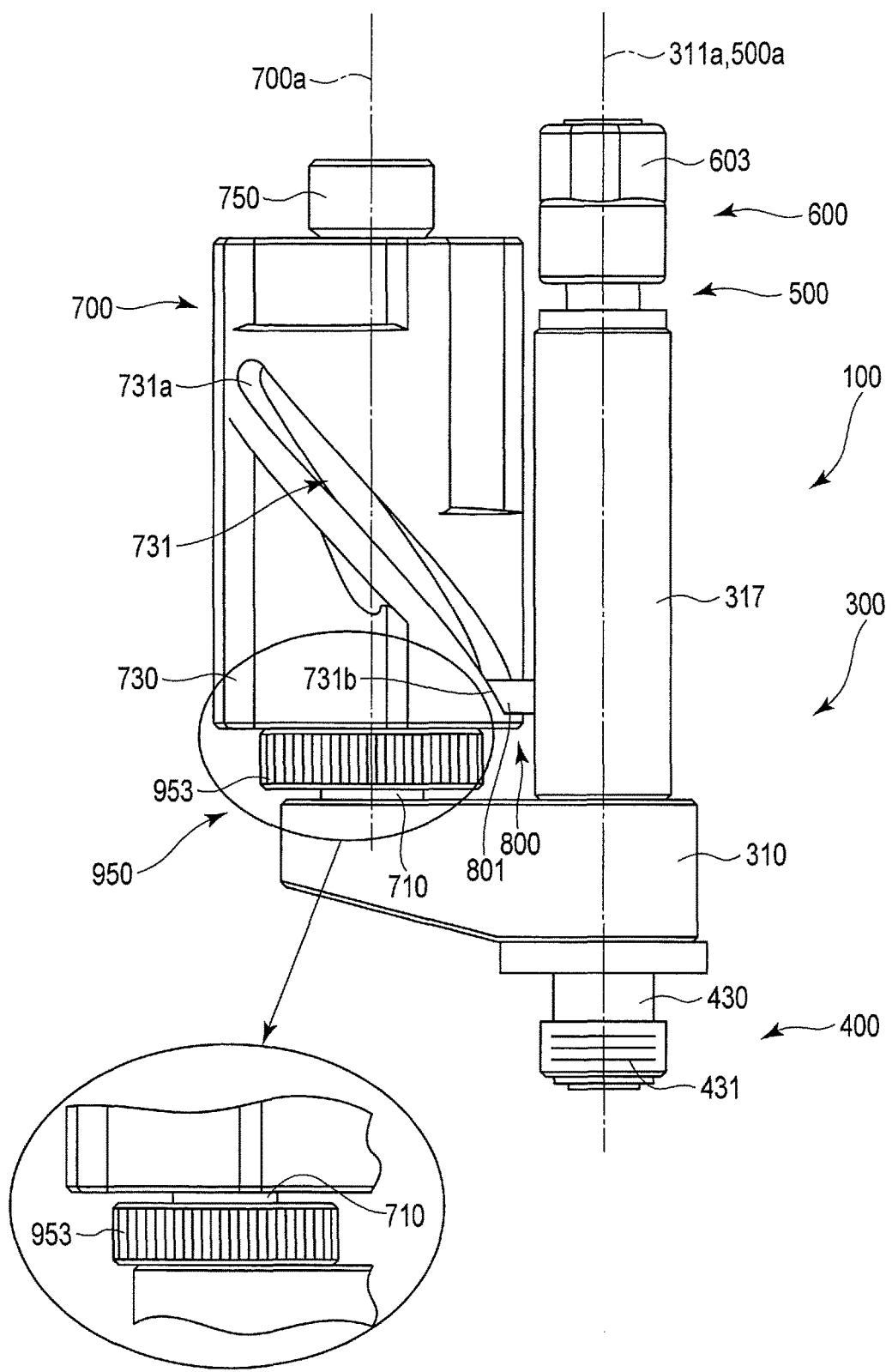
FIG. 7A is a diagram showing a first modification of a lock mechanism.
Figure 7B:
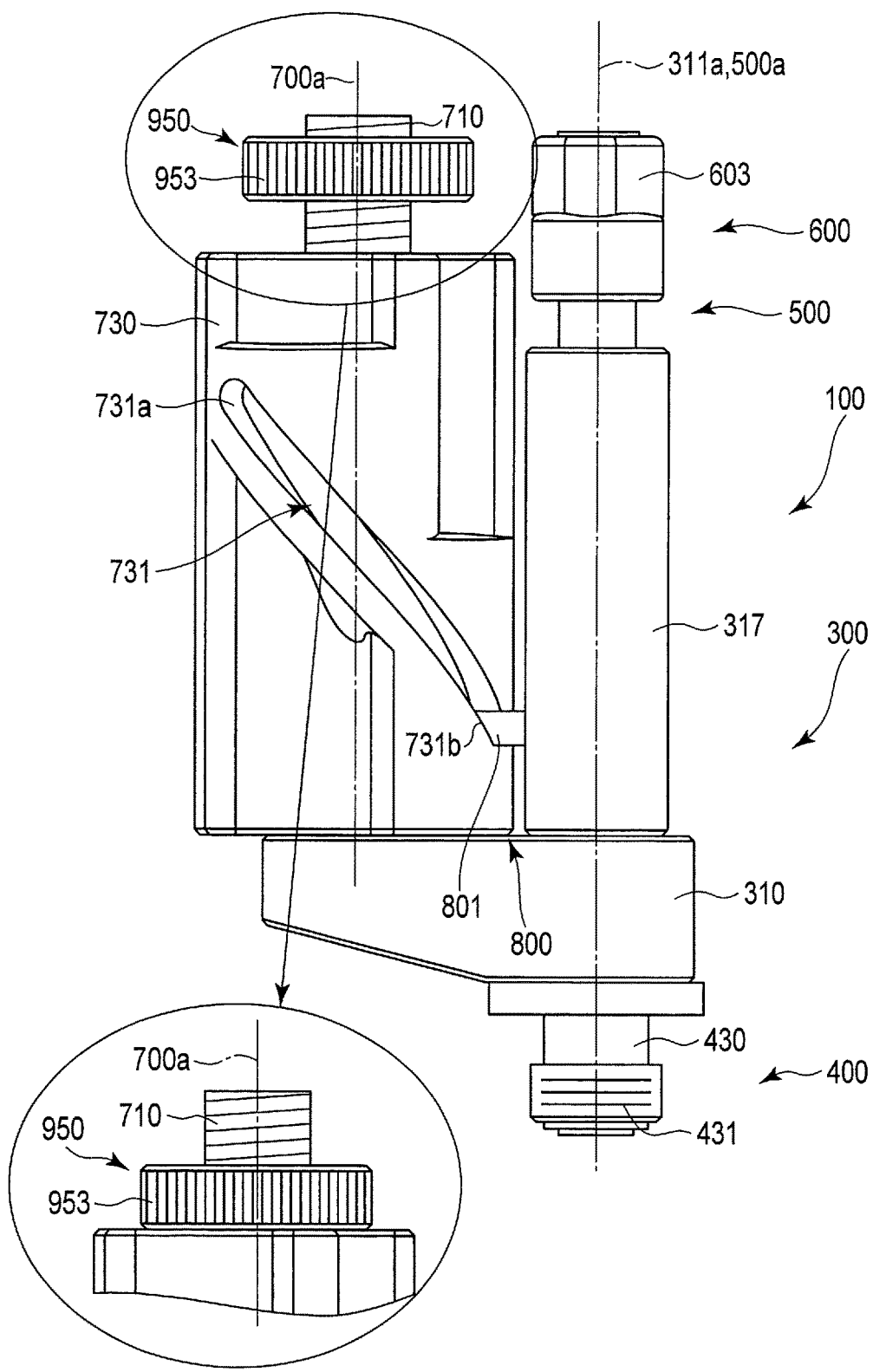
FIG. 7B is a diagram showing the first modification of the lock mechanism.

As shown in FIG. 7A and FIG. 7B, the lock mechanism 950 has a lock member 953 which is screwed (threaded) into the rotation shaft member 710 and which moves in the direction of the third central axis 700a to contact with the rotation body member 730 and thereby locks the rotation of the rotation body member 730.

As shown in FIG. 7A, the lock member 953 is screwed into the distal end portion of the rotation shaft member 710, and contacts with the distal face of the rotation body member 730 to lock the rotation of the rotation body member 730. As shown in FIG. 7B, the lock member 953 may be screwed into the proximal end portion of the rotation shaft member 710, and contacts with the proximal face of the rotation body member 730.

Thus, in the present modification, the treatment instrument 51 does not need to be fixed when the treatment instrument 51 has advanced to the maximum, in contrast with the first embodiment. In the present modification, the treatment instrument 51 can be fixed anywhere within the range of the advance and retreat operations of the treatment instrument 51 (within the advance and retreat range of the first tubular member 500).

[Second Modification of Lock Mechanism 950]

Figure 7C:
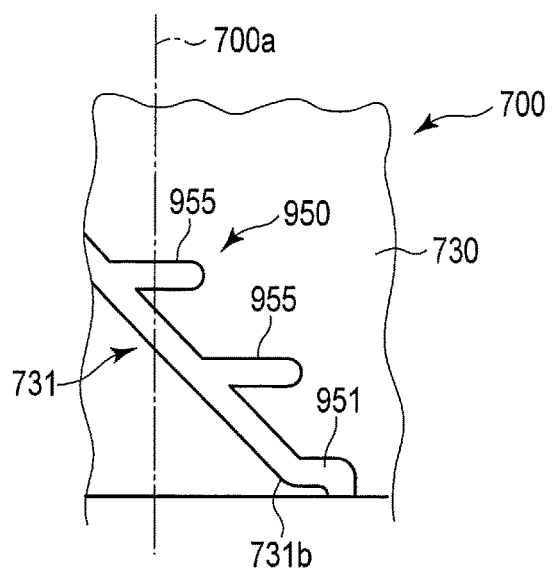
FIG. 7C is a diagram showing a second modification of the lock mechanism.

As shown in FIG. 7C, the lock mechanism 950 has a groove portion 955 which is provided in the outer circumferential surface of the rotation body member 730 to be in communication with the spiral groove portion 731 and which is provided along the direction around the third central axis 700a. For example, more than one groove portion 955 is provided, and the groove portions are provided a desired distance apart from each other in the direction of the third central axis 700a. The groove portions 955 are provided to avoid the recess portions 733. The groove portions 955 function as clearance grooves.

When the protrusion portion 801 is engaged with the groove portion 955, the lock mechanism 950 locks the rotation of the rotation body member 730.

Thus, in the present modification, the fixing position of the treatment instrument 51 can be set to a desired position in accordance with the position where the groove portion 955 is provided.

[Third Modification of Lock Mechanism 950]

Figure 7D:
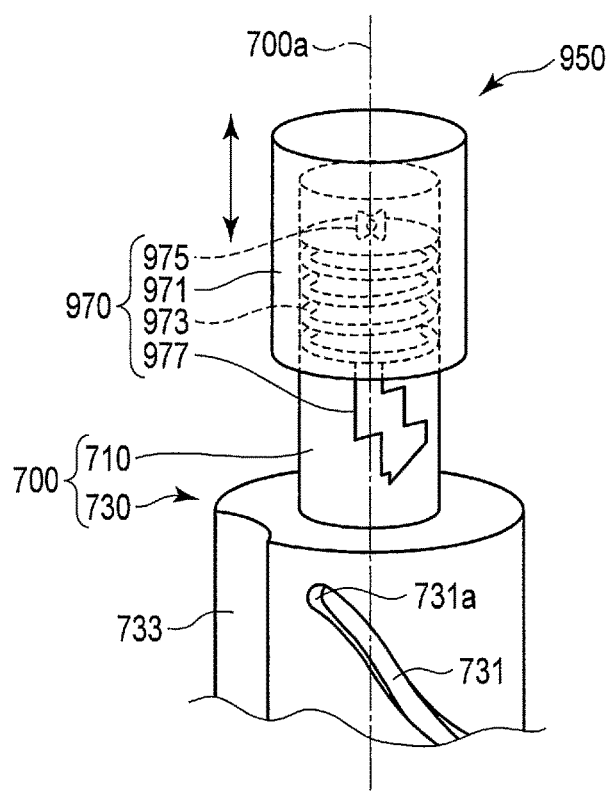
FIG. 7D is a diagram showing a third modification of the lock mechanism.

As shown in FIG. 7D, the lock mechanism 950 has a rotation cam mechanism 970.

As shown in FIG. 7D, the rotation cam mechanism 970 has a cap-shaped lock member 971 which is provided at the proximal end portion of the rotation shaft member 710 and which is movable along the direction of the third central axis 700a, and an urging member 973 which is provided inside the lock member 971 and which urges the lock member 971 to separate the lock member 971 from the proximal end portion of the rotation shaft member 710 along the direction of the third central axis 700a. The rotation cam mechanism 970 further has a cam member 975 provided inside the lock member 971, and a stepped groove portion 977 which is provided in the circumferential surface of the proximal end portion of the rotation shaft member 710 and with which the cam member 975 is removably engaged.

The urging member 973 has, for example, a coiled spring. The groove portion 977 is in communication with the outside so that the cam member 975 is inserted.

If the lock member 971 is pressed and then lowered in the direction of the third central axis 700a against the urging member 973, the cam member 975 is inserted into the groove portion 977, and the cam member 975 is engaged with an edge portion 977a of the groove portion 977, as shown in FIG. 7E. At the same time, the distal end portion of the lock member 971 abuts on the proximal end portion of the rotation body member 730, and the lock member 971 locks the rotation of the rotation body member 730. Since the cam member 975 is engaged with the edge portion 977a, the lock member 971 stays locked.

If the lock member 971 is pressed again, the cam member 975 is disengaged from the edge portion 977a as shown in FIG. 7F, and the urging member 973 separates the lock member 971 from the proximal end portion of the rotation shaft member 710 along the direction of the third central axis 700a. As a result, the rotation body member 730 becomes rotatable.

Thus, in the present modification, the treatment instrument 51 does not need to be fixed when the treatment instrument 51 has advanced to the maximum, in contrast with the first embodiment. In the present modification, the treatment instrument 51 can be fixed anywhere within the range of the advance and retreat operations of the treatment instrument 51 (within the advance and retreat range of the first tubular member 500).

[Fourth Modification of Lock Mechanism 950]

Figure 7G:
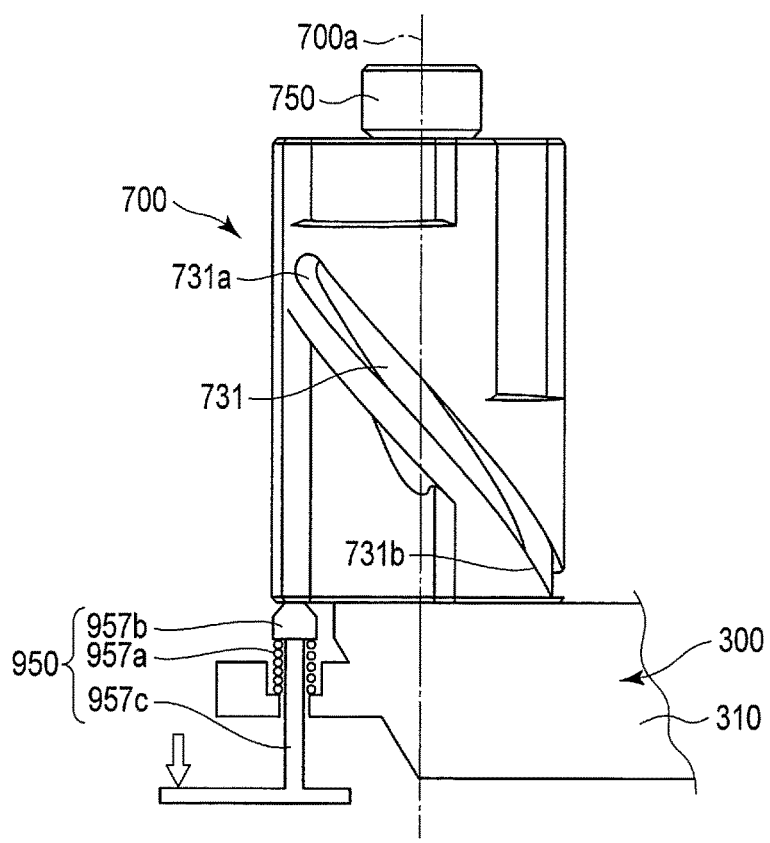
FIG. 7G is a diagram showing a fourth modification of the lock mechanism.

As shown in FIG. 7G, the lock mechanism 950 is provided in the base unit 300.

In this case, the lock mechanism 950 has an urging member 957a having an urging force to urge in the direction of the third central axis 700a, and a lock portion 957b which is urged toward the rotation body member 730 by the urging force to contact with the rotation body member 730 and thereby locks the rotation of the rotation body member 730. The lock mechanism 950 also has an operation portion 957c which is coupled to the lock portion 957b and which is operated to separate the lock portion 957b from the rotation body member 730 against the urging force when the rotation body member 730 rotates.

Thus, in the present modification, the treatment instrument 51 does not need to be fixed when the treatment instrument 51 has advanced to the maximum, in contrast with the first embodiment. In the present modification, the treatment instrument 51 can be fixed anywhere within the range of the advance and retreat operations of the treatment instrument 51 (within the advance and retreat range of the first tubular member 500).

[Fifth Modification of Lock Mechanism 950]

Figure 7H:
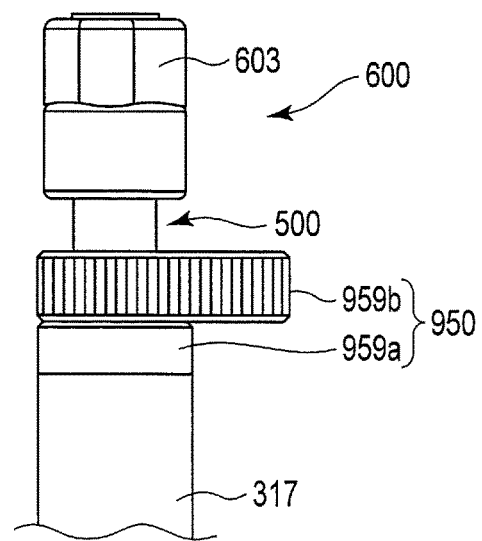
FIG. 7H is a diagram showing a fifth modification of the lock mechanism.

As shown in FIG. 7H, the lock mechanism 950 has a cylindrical elastic member 959a provided at the proximal end portion of the outer cylindrical portion 317, and a fastening portion 959b which is provided in the outer cylindrical portion 317 and which fastens the elastic member 959a to the first tubular member 500. The fastening portion 959 is, for example, a belt-shaped member.

Thus, in the present modification, the treatment instrument 51 does not need to be fixed when the treatment instrument 51 has advanced to the maximum, in contrast with the first embodiment. In the present modification, the treatment instrument 51 can be fixed anywhere within the range of the advance and retreat operations of the treatment instrument 51 (within the advance and retreat range of the first tubular member 500).

[First Modification of Attachment of Rotation Shaft Member 710 to Base Member 310]

Although the distal end portion of the rotation shaft member 710 is fitted into the depression portion 319 of the base member 310 and then fixed by the screw portion 213e in the first embodiment, the present invention does not need to be limited to this.

As shown in FIG. 8A, in the present modification, the distal end portion of the rotation shaft member 710 has a pair of protrusion portions 711a provided on the outer circumferential surface of the distal end portion. The protrusion portions 711a are provided, for example, symmetrically to each other.

The base member 310 has a pair of groove portions 319a which are provided in the inner circumferential surface of the depression portion 319 and into which the protrusion portions 711a fit. The groove portions 319a are provided, for example, symmetrically to each other. The groove portions 319a are, for example, L-shaped. For example, the short side of each of the groove portions 319a is provided along the axial direction of the depression portion 319, and is in communication with the outside in the direction of the third central axis 700a. For example, the long side of each of the groove portions 319a is provided along the circumferential direction of the depression portion 319. Lock portions 319b which lock the protrusions 711a are provided at the end portion of the long side. The lock portions 319b are, for example, protrusion portions.

The protrusions 711a fit into the groove portions 319a from the short sides of the groove portions 319a which are in communication with the outside. When the rotation shaft member 710 rotates around the third central axis 700a, the protrusions 711a slide on the long sides of the groove portions 319a. The protrusions 711a climb over the lock portions 319b which are the protrusion portions, and are thus engaged with the lock portions 319b. As a result, the rotation shaft member 710 is prevented from rotating around the third central axis 700a, and is fixed to the base member 310.

[Second Modification of Attachment of Rotation Shaft Member 710 to Base Member 310]

As shown in FIG. 8B, for example, a cylindrical elastic member 713 is attached to the distal end portion of the rotation shaft member 710. The elastic member 713 is made of, for example, a resin or rubber.

An edge portion 319e formed as an outer flange is provided around the depression portion 319.

As shown in FIG. 8B, when the distal end portion of the rotation shaft member 710 is fitted into the depression portion 319 of the base member 310, the elastic member 713 is caught on an edge 319c to cover the edge portion 319c. As a result, the rotation shaft member 710 is prevented from rotating around the third central axis 700a, and is fixed to the base member 310.

[Third Modification of Attachment of Rotation Shaft Member 710 to Base Member 310]

Figure 8C:
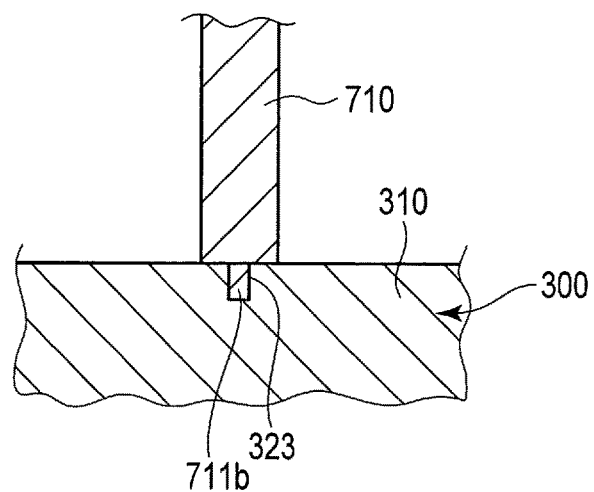
FIG. 8C is a diagram showing a third modification of the attachment of the rotation shaft member to the base member.

As shown in FIG. 8C, the rotation shaft member 710 has a protrusion portion 711b which is provided on a bottom surface of the rotation shaft member 710 and which protrudes downward of the rotation shaft member 710. The protrusion 711b is formed as, for example, a male socket.

As shown in FIG. 8C, the base member 310 has an opening portion 323 into which the protrusion portion 711b is put. The opening portion 323 is formed as, for example, a female socket.

When the protrusion portion 711b is put in the opening portion 323, the rotation shaft member 710 is prevented from rotating around the third central axis 700a, and is fixed to the base member 310.

[Fourth Modification of Attachment of Rotation Shaft Member 710 to Base Member 310]

Figure 8D:
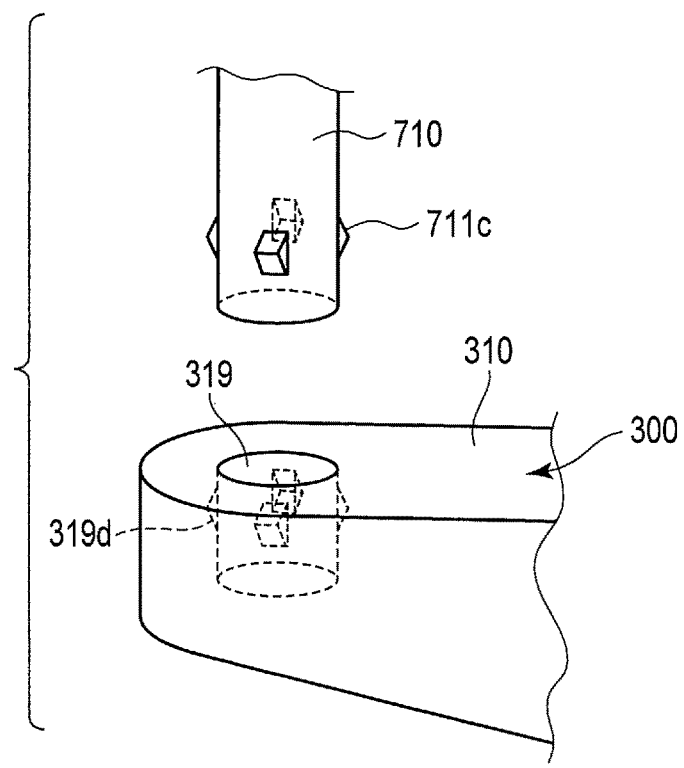
FIG. 8D is a diagram showing a fourth modification of the attachment of the rotation shaft member to the base member.

As shown in FIG. 8D, the distal end portion of the rotation shaft member 710 has protrusion portions 711c provided on the outer circumferential surface of the distal end portion. The protrusion portions 711c may be directly bonded to the outer circumferential surface, or may be fitted into unshown cutout portions formed in the outer circumferential surface. The protrusion portions 711c are provided, for example, a desired distance apart from each other. The protrusion portions 711c are made of an elastically deformable material such as a resin material.

As shown in FIG. 8D, the base member 310 has groove portions 319d which are provided in the inner circumferential surface of the depression portion 319 and into which the protrusions 711c fit. The groove portions 319d are provided, for example, a desired distance apart from each other.

When the distal end portion of the rotation shaft member 710 is fitted into the depression portion 319, the protrusions 711a are fitted into the groove portions 319d after elastically deformed. As a result, the rotation shaft member 710 is prevented from rotating around the third central axis 700a, and is fixed to the base member 310.

[First Modification of Rotation Body Member 730]

As shown in FIG. 9A, the rotation body member 730 is longer than the rotation body member 730 shown in the first embodiment in the direction of the third central axis 700a. Thus, in the present modification, even if the surgeon's hands are small, operability of the rotation body member 730 can be improved.

[Second Modification of Rotation Body Member 730]

Figure 9B:
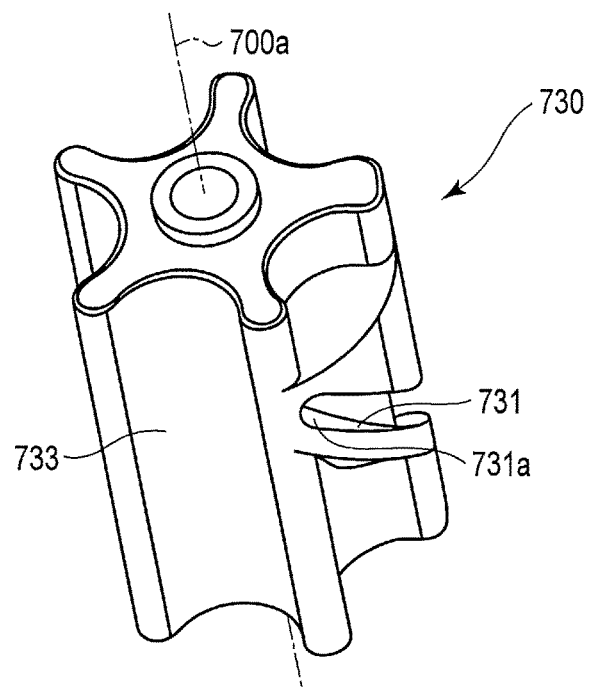
FIG. 9B is a diagram showing a second modification of the rotation body member.

As shown in FIG. 9B, a smaller number of recess portions 733 are provided than in the first embodiment. Thus, the circumferential surface of each of the recess portions 733 is wider than in the first embodiment. The inside diameter of each of the recess portions 733 is larger. Thus, in the present modification, even if the surgeon's fingers are wide, operability of the rotation body member 730 can be improved.

[Third Modification of Rotation Body Member 730]

Figure 9C:
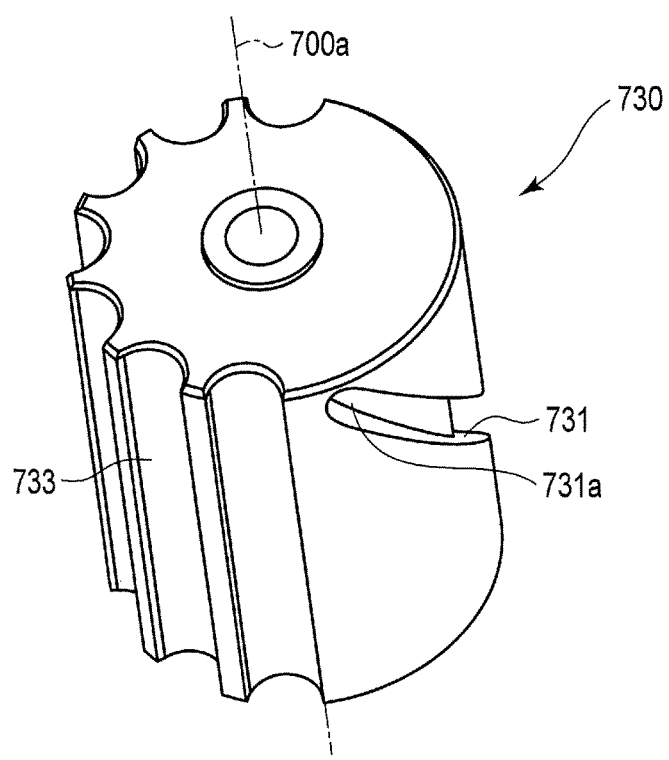
FIG. 9C is a diagram showing a third modification of the rotation body member.

As shown in FIG. 9C, a larger number of recess portions 733 are provided than in the first embodiment. Thus, the circumferential surface of each of the recess portions 733 is narrower than in the first embodiment. The inside diameter of each of the recess portions 733 is smaller. Thus, in the present modification, the rotation body member 730 can be easily operated by the ball of the finger.

[Fourth Modification of Rotation Body Member 730]

As shown in FIG. 9D, the rotation body member 730 is tapered from the proximal end portion of the rotation body member 730 toward the distal end portion of the rotation body member 730. Thus, in the present modification, the finger comes into good contact, and operability of the rotation body member 730 can be improved.

[Fifth Modification of Rotation Body Member 730]

As shown in FIG. 9E, the recess portions 733 are provided as domed cavities. Thus, in the present modification, the finger is better caught on the rotation body member 730, and operability of the rotation body member 730 can be improved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An advance and retreat assist tool for an endoscopic treatment instrument, the advance and retreat assist tool comprising:
    a base unit comprising a hole portion through which the endoscopic treatment instrument to be inserted into an endoscope passes;
    an attachment portion which attaches the base unit to a treatment instrument insertion portion of the endoscope so that the hole portion faces a treatment instrument insertion hole portion provided in the treatment instrument insertion portion;
    a tubular member provided to advance and retreat relative to the base unit coaxially with a central axis of the hole portion;
    a fixing portion which fixes the endoscopic treatment instrument to the tubular member;
    a rotary portion which has an axis different from an axis of the tubular member, which rotates around an axis of the rotary portion and which is operated by a finger of a hand of an operator grasping a grasping portion of the endoscope; and
    an advance and retreat mechanism comprising a protrusion portion which is provided along a diametrical direction of the tubular member and which is engaged with an outer circumferential surface of the tubular member, and a spiral groove portion which is spirally provided in an outer circumferential surface of the rotary portion to wind around the axis of the rotary portion and with which the protrusion portion is engaged, the advance and retreat mechanism converting a rotation force of the rotary portion during the rotation of the rotary portion to an advance and retreat force to advance and retreat the tubular member in an axial direction of the tubular member, the advance and retreat mechanism transmitting the advance and retreat force to the tubular member and thereby advancing and retreating the tubular member.

2. The advance and retreat assist tool for the endoscopic treatment instrument according to claim 1, wherein the attachment portion attaches the base unit to the treatment instrument insertion portion so that the base unit is rotatable around a central axis of the treatment instrument insertion hole portion.

3. The advance and retreat assist tool for the endoscopic treatment instrument according to claim 2, wherein the treatment instrument insertion portion having the treatment instrument insertion hole portion is provided in a grasping portion of the endoscope,
    a central axis direction of the treatment instrument insertion hole portion is slanted relative to a central axis direction of the grasping portion,
    a clearance is formed between the tubular member and the grasping portion,
    the rotary portion rotates around the axis of the rotary portion provided parallel to the axis of the tubular member, and
    when the base unit rotates around the central axis of the treatment instrument insertion hole portion, the rotary portion is provided inside the clearance closer to the grasping portion or provided outside the clearance away from the grasping portion.

4. The advance and retreat assist tool for the endoscopic treatment instrument according to claim 3, wherein the advance and retreat mechanism comprises
    a rotation prevention portion which prevents a rotation of the tubular member relative to the base unit.

5. The advance and retreat assist tool for the endoscopic treatment instrument according to claim 4, wherein the rotation prevention portion comprises
    an outer cylindrical portion which is provided in the base unit and into which the tubular member is inserted, and
    a long opening portion which is provided in the outer cylindrical portion along the axial direction of the tubular member, which the protrusion portion passes through in the diametrical direction of the tubular member to engage with the spiral groove portion, and which the protrusion portion slides along the axial direction of the tubular member.

6. The advance and retreat assist tool for the endoscopic treatment instrument according to claim 4, wherein the rotation prevention portion comprises
    a noncircular hollow portion of the tubular member, and
    a non-circular-cylindrical inner cylindrical portion which is provided in the base unit and which is fitted into the hollow portion.

7. The advance and retreat assist tool for the endoscopic treatment instrument according to claim 4, wherein the rotary portion comprises
    a rotation shaft member which has the axis of the rotary portion provided parallel to the axis of the tubular member and which is fixed to the base unit, and
    a rotation body member which is provided around the rotation shaft member and which rotates around the axis of the rotation shaft member, and
    the rotation body member comprises recess portions which are provided in an outer circumferential surface of the rotation body member to avoid the spiral groove portion and on which fingers of the hand of the operator grasping the grasping portion are put.

8. The advance and retreat assist tool for the endoscopic treatment instrument according to claim 7, wherein the rotary portion further comprises a coming-off prevention member which prevents the rotation body member from coming off the rotation shaft member.

9. The advance and retreat assist tool for the endoscopic treatment instrument according to claim 7, further comprising a lock mechanism which locks an inadvertent rotation of the rotation body member.

10. The advance and retreat assist tool for the endoscopic treatment instrument according to claim 1, wherein the attachment portion comprises a cylindrical body portion which is removably attached to the treatment instrument insertion portion so that the body portion is rotatable around a central axis of the treatment instrument insertion hole portion, and a cylindrical support portion which is attached to the body portion to support the base unit and which causes the hole portion to face the treatment instrument insertion hole portion so that the central axis of the hole portion is provided coaxially with the central axis of the treatment instrument insertion hole portion.

11. The advance and retreat assist tool for the endoscopic treatment instrument according to claim 10, wherein an edge portion of the treatment instrument insertion hole portion is provided between the support portion and the body portion in a direction of the central axis of the treatment instrument insertion hole portion, and the body portion presses the edge portion of the treatment instrument insertion hole portion into the support portion, and the attachment portion is fixed to the treatment instrument insertion portion.

12. The advance and retreat assist tool for the endoscopic treatment instrument according to claim 10, further comprising an interference prevention member which intervenes between the support portion and the edge portion of the treatment instrument insertion hole portion in a direction of the central axis of the treatment instrument insertion hole portion and which prevents interference between the support portion and the edge portion of the treatment instrument insertion hole portion.

13. The advance and retreat assist tool for the endoscopic treatment instrument according to claim 10, wherein the body portion comprises a cutout portion which is formed by a depression of a part of an edge portion of the body portion in a central axis direction of the body portion, and the body portion is pressed into the treatment instrument insertion portion from a side surface of the treatment instrument insertion portion via the cutout portion in a diametrical direction of the body portion, and is thereby attached to the treatment instrument insertion portion.

14. The advance and retreat assist tool for the endoscopic treatment instrument according to claim 5, further comprising a regulating mechanism which regulates the advance and retreat of the tubular member so that the tubular member moves between a part where the hole portion is in communication with the tubular member and a position on a side where the tubular member comes off an end of the outer cylindrical portion.

15. The advance and retreat assist tool for the endoscopic treatment instrument according to claim 14, wherein the outer cylindrical portion holds the tubular member so that the axis of the tubular member is provided coaxially with the central axis of the hole portion, so that the tubular member advances and retreats along an axis direction of the tubular member, and so that a movement of the tubular member in a direction that intersects at right angles with the axial direction is prevented.

* * * * *